(12) United States Patent
Deshpande et al.

(10) Patent No.: US 11,739,059 B2
(45) Date of Patent: *Aug. 29, 2023

(54) OXYGEN SCAVENGING MOLECULES, ARTICLES CONTAINING SAME, AND METHODS OF THEIR USE

(71) Applicant: Plastipak Packaging, Inc., Plymouth, MI (US)

(72) Inventors: Girish Nilkanth Deshpande, Morris Plains, NJ (US); Paul David Weipert, High Point, NC (US); Michael W. Ensley, Eden, NC (US)

(73) Assignee: Plastipak Packaging, Inc., Plymouth, MI (US)

( * ) Notice: Subject to any disclaimer, the term of this patent is extended or adjusted under 35 U.S.C. 154(b) by 47 days.

This patent is subject to a terminal disclaimer.

(21) Appl. No.: 17/164,148

(22) Filed: Feb. 1, 2021

(65) Prior Publication Data

US 2021/0403423 A1 Dec. 30, 2021

Related U.S. Application Data

(60) Continuation of application No. 16/189,363, filed on Nov. 13, 2018, now Pat. No. 10,906,870, which is a
(Continued)

(51) Int. Cl.
| | |
|---|---|
| *C07D 207/00* | (2006.01) |
| *C08K 5/00* | (2006.01) |
| *C07D 209/46* | (2006.01) |
| *C07D 209/48* | (2006.01) |
| *C07D 471/04* | (2006.01) |
| *C08K 5/098* | (2006.01) |
| *C08K 5/3417* | (2006.01) |
| *B65D 81/26* | (2006.01) |
| *B01J 20/06* | (2006.01) |
| *B01J 20/22* | (2006.01) |
| *B01J 20/26* | (2006.01) |
| *B65D 65/38* | (2006.01) |
| *C08K 5/3432* | (2006.01) |

(52) U.S. Cl.
CPC .......... *C07D 207/00* (2013.01); *B01J 20/06* (2013.01); *B01J 20/22* (2013.01); *B01J 20/262* (2013.01); *B65D 65/38* (2013.01); *B65D 81/266* (2013.01); *C07D 209/46* (2013.01); *C07D 209/48* (2013.01); *C07D 471/04* (2013.01); *C08K 5/00* (2013.01); *C08K 5/0091* (2013.01); *C08K 5/098* (2013.01); *C08K 5/3417* (2013.01); *C08K 5/3432* (2013.01); *C08K 2201/012* (2013.01)

(58) Field of Classification Search
CPC .. C07D 207/00; C07D 209/46; C07D 209/48; C07D 471/04; B01J 20/06; B01J 20/20; B01J 20/22; B01J 20/262; B65D 65/38; B65D 81/266; C08K 5/091; C08K 5/098
See application file for complete search history.

(56) References Cited

U.S. PATENT DOCUMENTS

| 2,841,591 A | 7/1958 | Prichard |
| 3,317,558 A | 5/1967 | Becke et al. |
| (Continued) |

FOREIGN PATENT DOCUMENTS

| AR | P080102003 | 5/2008 |
| AU | 2008251476 | 5/2008 |
| (Continued) |

OTHER PUBLICATIONS

Advisory Action dated May 19, 2014 for U.S. Appl. No. 12/893,817, filed Sep. 29, 2010 (Inventor—G. Deshpande; Applicant—Constar International, Inc.; pp. 1-9).
(Continued)

*Primary Examiner* — Edward J Cain
(74) *Attorney, Agent, or Firm* — Ballard Spahr LLP

(57) ABSTRACT

The invention relates to compounds of the structure of formula I and II:

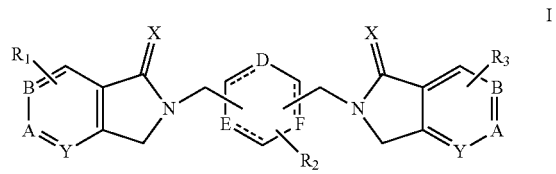

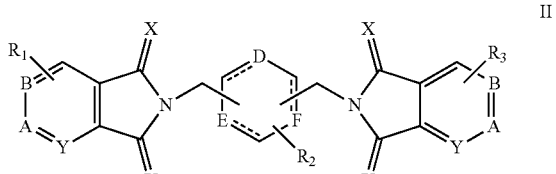

where X is selected from the group consisting of O, S and NH; Y, A and B are independently selected from the group consisting of N and CH; D, E and F are independently selected from the group consisting of CH, N, O and S; the symbol ---- represents a single or a double bond; and $R_1$, $R_2$ and $R_3$ are independently selected from the group consisting of H, electron withdrawing groups and electron releasing groups. In other embodiments, the compounds are used as oxygen scavengers and in barrier compositions and articles.

3 Claims, 5 Drawing Sheets

Related U.S. Application Data continuation of application No. 15/147,532, filed on May 5, 2016, now Pat. No. 10,125,096, which is a continuation of application No. 13/849,797, filed on Mar. 25, 2013, now Pat. No. 9,475,630, which is a continuation of application No. 13/164,477, filed on Jun. 20, 2011, now Pat. No. 8,431,721, which is a division of application No. 12/117,849, filed on May 9, 2008, now Pat. No. 7,994,245.

(60) Provisional application No. 60/928,553, filed on May 10, 2007.

(56) References Cited

U.S. PATENT DOCUMENTS

| | | | |
|---|---|---|---|
| 3,322,785 | A | 5/1967 | Fletcher |
| 4,536,409 | A | 8/1985 | Farrell et al. |
| 4,769,444 | A | 9/1988 | Joswig et al. |
| 4,786,671 | A | 11/1988 | Kress et al. |
| 5,021,515 | A | 6/1991 | Cochran et al. |
| 5,049,624 | A | 9/1991 | Adams et al. |
| 5,075,362 | A | 12/1991 | Hofeldt et al. |
| 5,116,547 | A | 5/1992 | Tsukahara et al. |
| 5,211,875 | A | 5/1993 | Speer et al. |
| 5,250,592 | A | 10/1993 | Nesvadba |
| 5,639,815 | A | 6/1997 | Cochran et al. |
| 5,955,527 | A | 9/1999 | Cochran et al. |
| 6,261,749 | B1 | 7/2001 | Asami |
| 6,610,234 | B2 | 8/2003 | Akkapeddi et al. |
| 6,780,916 | B2 | 8/2004 | Tung et al. |
| 7,691,290 | B2 | 4/2010 | Deshpande et al. |
| 7,879,930 | B2 | 2/2011 | Liu |
| 7,994,245 | B2 * | 8/2011 | Deshpande ............ C08K 5/098 524/92 |
| 8,431,721 | B2 * | 4/2013 | Deshpande ............ C08K 5/00 524/92 |
| 8,450,398 | B2 | 5/2013 | Deshpande |
| 8,721,920 | B2 | 5/2014 | Deshpande et al. |
| 8,748,519 | B2 | 6/2014 | Deshpande |
| 8,975,345 | B2 | 3/2015 | Deshpande |
| 9,181,414 | B2 | 11/2015 | Deshpande |
| 9,222,020 | B2 | 12/2015 | Deshpande |
| 9,475,630 | B2 * | 10/2016 | Deshpande ............ C08K 5/00 |
| 10,125,096 | B2 * | 11/2018 | Deshpande .......... C07D 209/48 |
| 10,988,589 | B2 * | 4/2021 | Teranishi ............ C08K 5/3445 |
| 2003/0109643 | A1 | 6/2003 | Ching et al. |
| 2004/0241468 | A1 | 12/2004 | Otaki |
| 2006/0069197 | A1 | 3/2006 | Tammaji et al. |
| 2006/0128861 | A1 | 6/2006 | Stewart et al. |
| 2006/0180790 | A1 | 8/2006 | Deshpande et al. |
| 2006/0182911 | A1 | 8/2006 | Tammaji et al. |
| 2006/0247388 | A1 | 11/2006 | Hale et al. |
| 2007/0066731 | A1 | 3/2007 | Tattum et al. |
| 2007/0241309 | A1 | 10/2007 | Uradnisheck |
| 2008/0161472 | A1 | 7/2008 | Jenkins et al. |
| 2008/0241521 | A1 | 10/2008 | Solovyov et al. |
| 2008/0255280 | A1 | 10/2008 | Sims et al. |
| 2008/0277622 | A1 | 11/2008 | Deshpande et al. |
| 2009/0030115 | A1 | 1/2009 | Liu |
| 2009/0278087 | A1 | 11/2009 | Deshpande et al. |
| 2010/0154361 | A1 | 6/2010 | Deshpande et al. |
| 2011/0171405 | A1 | 7/2011 | Deshpande |
| 2011/0172335 | A1 | 7/2011 | Deshpande |
| 2011/0251395 | A1 | 10/2011 | Deshpande et al. |
| 2011/0275750 | A1 | 11/2011 | Bene et al. |
| 2012/0095144 | A1 | 4/2012 | Roelofs et al. |
| 2012/0175555 | A1 | 7/2012 | Menozzi et al. |
| 2012/0199515 | A1 | 8/2012 | Peters et al. |
| 2012/0283366 | A1 | 11/2012 | Akkapeddi et al. |
| 2013/0158182 | A1 | 6/2013 | Menozzi et al. |

FOREIGN PATENT DOCUMENTS

| | | |
|---|---|---|
| AU | 2008251476 A1 | 11/2008 |
| AU | 2010303748 | 9/2010 |
| AU | 2010319298 | 11/2010 |
| AU | 2010319302 | 11/2010 |
| AU | 2010319384 | 11/2010 |
| AU | 2018204862 | 11/2010 |
| AU | 2018204870 | 11/2010 |
| AU | 2014224080 | 9/2014 |
| AU | 2016200734 | 2/2016 |
| AU | 2016200891 | 2/2016 |
| AU | 2016203377 | 5/2016 |
| AU | 201673939 | 12/2016 |
| AU | 2017200010 | 1/2017 |
| AU | 2019203479 | 11/2019 |
| BR | PI0810744.0 | 5/2008 |
| CA | 1272341 A1 | 7/1990 |
| CA | 2247985 A1 | 9/1997 |
| CA | 2687081 | 5/2008 |
| CA | 2779714 | 9/2010 |
| CA | 2780746 | 11/2010 |
| CA | 2780749 | 11/2010 |
| CA | 2780768 | 11/2010 |
| CA | 2780768 | 5/2011 |
| CL | 1391/2008 | 5/2008 |
| CN | 101072820 A | 11/2007 |
| CN | 200880023116.X | 5/2008 |
| CN | 101193976 A | 6/2008 |
| CN | 101688020 A | 3/2010 |
| CN | 2013106426272 | 12/2013 |
| DE | 134980 C | 10/1901 |
| DE | 442774 C | 4/1927 |
| EP | 0144807 A2 | 6/1985 |
| EP | 1442993 A1 | 8/2004 |
| EP | 08795847.6 | 5/2008 |
| EP | 10822439.5 | 9/2010 |
| EP | 10830816.4 | 11/2010 |
| EP | 10830818.0 | 11/2010 |
| EP | 10830821.4 | 11/2010 |
| EP | 2483342 A2 | 8/2012 |
| EP | 14150235.1 | 1/2014 |
| EP | 21195379.9 | 11/2020 |
| GB | 1490671 A | 11/1977 |
| HK | 10107172.3 | 7/2010 |
| HK | 15100461.3 | 1/2015 |
| IN | 11396/DELNP/2015 | 12/2015 |
| IN | 11397/DELNP/2015 | 12/2015 |
| IN | 7423/DELNP/2009 | 7/2016 |
| JP | H01-026667 A | 1/1989 |
| JP | 2005008867 A | 1/2005 |
| JP | 2010-507697 | 5/2008 |
| JP | 2017-101689 | 5/2008 |
| JP | 2008523170 A | 7/2008 |
| JP | 2013-105954 | 5/2013 |
| JP | 5697445 | 4/2015 |
| JP | 2015-249201 | 12/2015 |
| JP | 2016040389 | 3/2016 |
| JP | 5944861 | 7/2016 |
| KR | 10-2009-7025208 | 5/2008 |
| MX | MX/a/2009/012183 | 5/2008 |
| MX | MX/a/2013/001496 | 2/2013 |
| RU | 2307846 C2 | 10/2007 |
| RU | 2009145713 | 5/2008 |
| RU | 2406741 C2 | 12/2010 |
| RU | 2009145713 A | 6/2011 |
| RU | 2013142425 | 9/2013 |
| TW | 097117502 | 5/2008 |
| TW | 103123705 | 7/2014 |
| VE | 2008-000929 | 5/2008 |
| WO | WO-1995/002616 A2 | 1/1995 |
| WO | WO-2003/109643 | 6/2003 |
| WO | WO-2004/063247 A1 | 7/2004 |
| WO | WO-2005/073272 A1 | 8/2005 |
| WO | WO-2006/062816 A2 | 6/2006 |
| WO | WO-2006/088889 A2 | 8/2006 |
| WO | PCT/US2008/0632 | 5/2008 |
| WO | WO-2008/141185 A1 | 11/2008 |
| WO | WO-2009/152114 A1 | 12/2009 |
| WO | PCT/US2010/050719 | 9/2010 |
| WO | PCT/US2010/056585 | 11/2010 |
| WO | PCT/US2010/056598 | 11/2010 |

(56) References Cited

FOREIGN PATENT DOCUMENTS

| WO | WO-2013/165971 A1 | 11/2013 |
|---|---|---|
| WO | PCT/US2010/056594 | 11/2020 |
| ZA | 2009/08083 | 5/2008 |

OTHER PUBLICATIONS

Amendment and Response to Final Office Action after Notice of Appeal filed on May 1, 2014 for U.S. Appl. No. 12/893,817, filed Sep. 29, 2010 and published as US 2011-0123741 A1 on May 26, 2011 (Inventor—G. Deshpande; Applicant—Constar International, Inc.; pp. 1-20).
Amendment/Request for Re-consideration after Non Final Rejection dated Jul. 11, 2016 to the U.S. Patent and Trademark Office for U.S. Appl. No. 12/893,817, filed Sep. 29, 2010 and published as US 2011-0123741 A1 on May 26, 2011 (Inventor—Girish N. Deshpande) (39 pages).
Amendment/Request for Re-consideration after Non Final Rejection dated Sep. 4, 2015 to the U.S. Patent and Trademark Office for U.S. Appl. No. 12/893,817, filed Sep. 29, 2010 and published as US 2011-0123741 A1 on May 26, 2011 (Inventor—Girish N. Deshpande) (19 pages).
Bandi, S. et al., The mechanism of color generation in poly(ethylene terephthalate) / polyamide blends, Polymer Degradation and Stability, 2005, 88: pp. 341-348.
Buhleier, E., et al., 2,6-Bis(aminomethyl)pyridine als Komplexligand und neues Kronenethersynthon, Justus Liebigs Annalen der Chemie, 1978, No. 4: pp. 537-544.
Böhme, H. et al., Untersuchungen in der Phthalimidin-Reihe, Die Pharmazie, 1970, 25: pp. 283-289.
Chen et al., Efficient enhancement of DNA cleavage activity by introducing guanidinium groups into diiron(III) complex, Bioorganic & Medicinal Chemistry Letters, Pergamon, Elsevier Science, GB, vol. 18, No. 1, Nov. 5, 2007 (Nov. 5, 2007), pp. 109-113.
Communication pursuant to Article 94(3) EPC dated May 28, 2015 for EP Pat. App. No. 14150235.1, filed Jan. 6, 2014 (Inventor—G. Deshpande et al.; Applicant—Constar International, Inc.; pp. 1-4).
Communication pursuant to Article 94(3) EPC dated Mar. 18, 2016 for EP Pat. App. No. 14150235.1, filed Jan. 6, 2014 (Inventor—G. Deshpande et al.; Applicant—Constar International, Inc.; pp. 1-2).
Communication pursuant to Article 94(3) EPC dated Apr. 14, 2014 for EP Pat. App. No. 10830816.4, filed Nov. 12, 2010 and published as 2499134 on Sep. 19, 2012 (Inventor—G. Deshpande et al.; pp. 1-2).
Communication pursuant to Article 94(3) EPC dated Jun. 19, 2015 for EP Pat. App. No. 10830816.4, filed Nov. 12, 2010 and published as 2499134 on Sep. 19, 2012 (Inventor—G. Deshpande et al.; pp. 1-2).
Communication under Rule 71(3) EPC dated Sep. 7, 2016 for EP Pat. App. No. 10822439.5, filed Sep. 29, 2010 (Inventor—G. Deshpande et al.; Applicant—Constar International, Inc.; pp. 1-67).
Database PubChem Compound [Online], NCBI; (Sep. 7, 2005), XP002724996, Database accession No. CID 3317391.
European Search Opinion dated Aug. 27, 2015 by the European Patent Office for Application No. 10830821.4, which was filed on Nov. 12, 2010 and published as 2499182 on Sep. 19, 2012 (Inventor—Girish N. Deshpande) (5 pages).
Office Action dated Oct. 25, 2019 by the European Patent Office for EP Application No. 10830821.4, filed on Nov. 12, 2010 and published as EP 2499182 on Sep. 19, 2012 (Applicant—Plastipak Packaging, Inc.) (4 Pages).
Examination Report dated Sep. 20, 2012 for AU Pat. App. No. 2008251476, national phase of Intl. App. No. PCT/US2008/063250, filed May 9, 2008 (Inventor—G. Deshpande et al.; Applicant—Constar International, Inc.; pp. 1-3).
Examination Report dated Sep. 10, 2015 by the Australian Patent Office for Australian Application No. 2010303748, which was filed on Sep. 29, 2010 (Inventor—Girish N. Deshpande) (2 pages).
Examination Report dated Sep. 4, 2015 by the Australian Patent Office for Australian Application No. 2010319384, which was filed on Nov. 12, 2010 (Inventor—Girish N. Deshpande) (4 pages).
Examiner Initiated Interview Summary dated Nov. 18, 2014 for U.S. Appl. No. 12/945,351, filed Nov. 12, 2010 (Inventor—G. Deshpande; Applicant—Constar International, Inc.; pp. 1-1).
Examiner Initiated Interview Summary dated Dec. 12, 2014 for U.S. Appl. No. 12/893,817, filed Sep. 29, 2010 (Inventor—G. Deshpande; Applicant—Constar International, Inc.; pp. 1-3).
Ex Parte Quayle Action was issued on Nov. 5, 2015 by the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (5 pages).
Extended European Search Report dated Mar. 9, 2013 for EP Pat. App. No. 10830816.4, and published as 2499134 on Sep. 19, 2012 (Inventor—G. Deshpande; Applicant—Constar International, Inc.; pp. 1-7).
Extended European Search Report dated Jun. 17, 2014 for EP Pat. App. No. 14150235.1, filed Jan. 6, 2014 (Inventor—G. Deshpande et al.; Applicant—Constar International, Inc.; pp. 1-9).
Final Office Action dated May 7, 2014 for U.S. Appl. No. 12/945,351, filed Nov. 12, 2010 (Inventor—G. Deshpande; Applicant—Constar International, Inc.; pp. 1-6).
Final Office Action dated Jun. 19, 2014 for U.S. Appl. No. 13/849,797, filed Mar. 25, 2013 (Inventor—G. Deshpande et al.; Applicant—Constar International, Inc.; pp. 1-4).
Final Office Action dated Nov. 1, 2013 for U.S. Appl. No. 12/893,817, filed Sep. 29, 2010 (Inventor—G. Deshpande; Applicant—Constar International, Inc.; pp. 1-10).
Final Rejection dated Aug. 29, 2016 to the U.S. Patent and Trademark Office for U.S. Appl. No. 12/893,817, filed Sep. 29, 2010 and published as US 2011-0123741 A1 on May 26, 2011 (Inventor—Girish N. Deshpande) (5 pages).
First Examination Report dated Dec. 19, 2014 for Indian Application No. 7423/DELNP/2009, which was filed on May 9, 2008 (Inventor—G. Deshpande et al.) (pp. 1-2).
First Office Action dated Dec. 11, 2015 for Chinese Application No. 2013106426272, which was filed on Dec. 3, 2013 and published as CN104017241 on Sep. 3, 2014 (Inventor—G. Deshpande et al.; Applicant—Constar International, Inc.; Original—3 pages// Translated—6 pages).
First Office Action dated Jul. 6, 2011 for CN Pat. App. No. 200880023116.X, which is national phase of Intl. App. No. PCT/US2008/063250, filed May 9, 2008 (Inventor—G. Deshpande et al.; Applicant—Constar International, Inc.; pp. 1-7).
First Office Action dated Apr. 1, 2015 by the Canadian Patent Office for Canadian Application No. 2687081, which was filed on May 9, 2008 (Inventor—Girish N. Deshpande) (3 pages).
First Office Action dated Jun. 30, 2016 by the Japanese Patent Office for Japanese Application No. 2015-249201, which was filed on Dec. 22, 2015 (Inventor—Girish N. Deshpande et al) (Original 2 pages// Translated 2 pages).
Grawe, T. et al., Self-Assembly of Ball-Shaped Molecular Complexes in Water, Journal of Organic Chemistry, 2002, vol. 67(11): pp. 3755-3763.
Hu, Y.S. et al., Improving Transparancy of stretched PET/MXD6 blends by modifying PET with isophthalate, Polymer, Elsevier Science, vol. 46 No. 14 Jun. 2005 pp. 5202-5210.
International Preliminary Report on Patentability dated Apr. 12, 2012 for Intl. App. No. PCT/US2010/050719, dated Sep. 29, 2010 (Inventor—G. Deshpande; Applicant—Constar International, Inc.; pp. 1-5).
International Preliminary Report on Patentability dated May 24, 2012 for Intl. App. No. PCT/US2010/056585, dated Nov. 12, 2010 (Inventor—G. Deshpande; Applicant—Constar International, Inc.; pp. 1-6).
International Preliminary Report on Patentability dated May 24, 2012 for Intl. App. No. PCT/US2010/056594, dated Nov. 12, 2010 (Inventor—G. Deshpande; Applicant—Constar International, Inc.; pp. 1-5).

(56) References Cited

OTHER PUBLICATIONS

International Preliminary Report on Patentability dated May 24, 2012 for Intl. App. No. PCT/US2010/056598, dated Nov. 12, 2010 (Inventor—G. Deshpande; Applicant—Constar International, Inc.; pp. 1-7).
International Preliminary Report on Patentability dated Nov. 10, 2009 for Intl. App. No. PCT/US2008/063250, filed May 9, 2008 (Inventor—G. Deshpande et al.; Applicant—Constar International, Inc.; pp. 1-7).
International Search Report with Written Opinion dated Oct. 29, 2008 for Intl. App. No. PCT/US2008/063250, filed May 9, 2008 (Inventor—G. Deshpande et al.; Applicant—Constar International, Inc.; pp. 1-14).
International Search Report with Written Opinion dated Jun. 27, 2011 for Intl. App. No. PCT/US2010/050719, dated Sep. 29, 2010 (Inventor—G. Deshpande; Applicant—Constar International, Inc.; pp. 1-7).
International Search Report with Written Opinion dated Jul. 25, 2011 for Intl. App. No. PCT/US2010/056585, dated Nov. 12, 2010 (Inventor—G. Deshpande; Applicant—Constar International, Inc.; pp. 1-8).
International Search Report with Written Opinion dated Jul. 28, 2011 for Intl. App. No. PCT/US2010/056594, dated Nov. 12, 2010 (Inventor—G. Deshpande; Applicant—Constar International, Inc.; pp. 1-8).
International Search Report with Written Opinion dated Aug. 2, 2011 for Intl. App. No. PCT/US2010/056598, dated Nov. 12, 2010 (Inventor—G. Deshpande; Applicant—Constar International, Inc.; pp. 1-13).
Issue Notification dated Oct. 21, 2015 for U.S. Appl. No. 12/945,351, filed Nov. 12, 2010 (Inventor—G. Deshpande; Applicant—Constar International, Inc.; pp. 1-7).
Issue Notification dated Feb. 18, 2015 for U.S. Appl. No. 12/258,823, filed Apr. 22, 2014 (Inventor—G. Deshpande; Applicant—Constar International, Inc.; 1 page).
Issue Notification dated May 21, 2014 for U.S. Appl. No. 12/945,353, filed Nov. 12, 2010 (Inventor—G. Deshpande; Applicant—Constar International, Inc.; 1 page).
Issue Notification dated May 8, 2013 for U.S. Appl. No. 12/945,355, filed Nov. 12, 2010 (Inventor—G. Deshpande et al.; Applicant—Constar International, LLC; 1 page).
Issue Notification dated Oct. 5, 2016 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (1 pages).
Keenan, R.M. et al., Conformational Preferences in a Benzodiazepine Series of Potent Nonpeptide Fibrinogen Receptor Antagonists, Journal of Medicinal Chemistry, 1999, vol. 42(4): pp. 545-559.
Kricheldorf, H.R., 15N NMR Spectroscopy 28-Solvent Effects on the 15N-13C Coupling Constants of Amides, Imides, Ureas and Polypeptides, OMR Organic Magnetic Resonance, 1980, vol. 14(6): pp. 455-561.
Knollmüller, M. 1,2,4,5-Tetrahydro-3,2,4-benzothiadiazepin-3,3-dioxide und 1,2,3,5,6,7-Hexahydro-4,3,5-benzothiadiazonin-4,4-dioxide, Monatshefte für Chemie, 1974, 105, pp. 114-122.
Mauro Vieira de Almeida et al., Thalidomide Analogs from Diamines: Synthesis and Evaluation as Inhibitors of TNF-[alpha] Production, Chemical & Pharmaceutical Bulletin, 2007, vol. 55(2): pp. 223-226.
Non Final Office Action dated Feb. 14, 2013 for U.S. Appl. No. 12/893,817, filed Sep. 29, 2010 and published as US 2011-0123741 A1 on May 26, 2011 (Inventor—G. Deshpande et al.; Applicant—Constar International, Inc.; pp. 1-8).
Non Final Rejection dated Jan. 11, 2016 by the U.S. Patent and Trademark Office for U.S. Appl. No. 12/893,817, filed Sep. 29, 2010 and published as US 2011-0123741 A1 on May 26, 2011 (Inventor—Girish N. Deshpande) (11 pages).
Non Final Rejection dated Sep. 30, 2016 to the U.S. Patent and Trademark Office for U.S. Appl. No. 14/585,413, filed Dec. 30, 2014 (Inventor—Girish N. Deshpande) (pp. 1-8).

Non-Final Office Action dated Mar. 4, 2015 for U.S. Appl. No. 12/893,817, filed Sep. 29, 2010 and published as US 2011-0123741 A1 on May 26, 2011 (Inventor—G. Deshpande; Applicant—Constar International, Inc.; pp. 1-9).
Non-Final Office Action dated Apr. 29, 2013 for U.S. Appl. No. 12/945,353, filed Nov. 12, 2010 (Inventor—G. Deshpande; Applicant—Constar International, Inc.; pp. 1-8).
Non-Final Office Action dated Sep. 3, 2013 for U.S. Appl. No. 12/945,351, filed Nov. 12, 2010 (Inventor—G. Deshpande; Applicant—Constar International, Inc.; pp. 1-6).
Non-Final Office Action dated Jan. 20, 2011 for U.S. Appl. No. 12/117,849, filed May 9, 2008 (Inventor—G. Deshpande et al.; Applicant—Constar International, Inc.; pp. 1-5).
Non-Final Office Action dated Nov. 18, 2014 for U.S. Appl. No. 12/945,351, filed Nov. 12, 2010 (Inventor—G. Deshpande; Applicant—Constar International, Inc.; pp. 1-6).
Non-Final Office Action dated Dec. 5, 2013 for U.S. Appl. No. 13/849,797, filed Mar. 25, 2013 (Inventor—G. Deshpande et al.; Applicant—Constar International, Inc.; pp. 1-6).
Notice of Allowance dated Jan. 16, 2013 for U.S. Appl. No. 12/945,355, filed Nov. 12, 2010 (Inventor—G. Deshpande et al.; Applicant—Constar International, LLC; pp. 1-5).
Notice of Allowance dated Jan. 22, 2014 for U.S. Appl. No. 12/945,353, filed Nov. 12, 2010 (Inventor—G. Deshpande; Applicant—Constar International, Inc.; pp. 1-5).
Notice of Allowance dated Jun. 30, 2015 for U.S. Appl. No. 12/945,351, filed Nov. 12, 2010 (Inventor—G. Deshpande; Applicant—Constar International, Inc.; pp. 1-7).
Notice of Allowance dated Sep. 26, 2012 for U.S. Appl. No. 12/945,355, filed Nov. 12, 2010 (Inventor—G. Deshpande et al.; Applicant—Constar International, LLC; pp. 1-19).
Notice of Allowance dated Oct. 2, 2014 for U.S. Appl. No. 12/258,823, filed Apr. 22, 2014 (Inventor—G. Deshpande; Applicant—Constar International, Inc.; pp. 1-14).
Notice of Allowance dated Dec. 23, 2011 for U.S. Appl. No. 13/164,477, filed Jun. 20, 2011 (Inventor—G. Deshpande et al.; Applicant—Constar International, Inc.; pp. 1-8).
Notice of Allowance dated Feb. 10, 2015 for U.S. Appl. No. 12/258,823, filed Apr. 22, 2014 (Inventor—G. Deshpande; Applicant—Constar International, Inc.; pp. 1-2).
Notice of Allowance dated Jun. 24, 2011 for U.S. Appl. No. 12/117,849, filed May 9, 2008 (Inventor—G. Deshpande et al.; Applicant—Constar International, Inc.; pp. 1-7).
Notice of Allowance dated Jan. 20, 2016 by the Canadian Patent Office for Canadian Application No. 2687081 which was filed on May 9, 2008 (Inventor—Girish N. Deshpande) (1 page).
Notice of Allowance dated Jan. 5, 2016 by the Taiwan Patent Office for Taiwan Application No. 103123705 which was filed on Jul. 19, 2014 and published as 201439163 on Oct. 16, 2014 (Inventor—Girish N. Deshpande) (3 pages).
Notice of Allowance dated Jun. 8, 2016 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (7 pages).
Notice of Appeal filed on May 1, 2014 for U.S. Appl. No. 12/893,817, filed Sep. 29, 2010 (Inventor—G. Deshpande; Applicant—Constar International, Inc.; pp. 1-1).
Notice of Appeal was mailed on Dec. 19, 2014 to the U.S. Patent and Trademark Office for U.S. Appl. No. 13/849,797, filed on Mar. 25, 2013 and published as US-2014-0027339-A1 on Jan. 30, 2014 (Inventor—Girish N. Deshpande) (2 pages).
Office Action dated Apr. 19, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-2).
Office Action dated Sep. 30, 2011 for CL Pat. App. No. 1391-08, national phase of Intl. App. No. PCT/US2008/063250, filed May 9, 2008 (Inventor—G. Deshpande et al.; Applicant—Constar International, Inc.; pp. 1-21).
Office Action dated Sep. 23, 2011 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-3).

(56) References Cited

OTHER PUBLICATIONS

Office Action dated Mar. 30, 2015 by the Taiwan Patent Office for Taiwan Application No. 103123705 which was filed on Jul. 19, 2014 and published as 201439163 on Oct. 16, 2014 (Inventor—Girish N. Deshpande) (10 pages).
Office Action dated Apr. 21, 2016 by the Canadian Patent Office for Canadian Application No. 2779714, which was filed on Sep. 29, 2010 (Inventor—Girish N. Deshpande) (3 pages).
Office Action dated Jul. 27, 2016 by the Canadian Patent Office for Canadian Application No. 2,780,768, which was filed on Nov. 12, 2010 (Inventor—Girish N. Deshpande) (4 pages).
Office Action dated Sep. 13, 2016 by the Canadian Patent Office for Canadian Application No. 2,780,746, which was filed on Nov. 12, 2010 (Inventor—Girish N. Deshpande) (4 pages).
Preliminary Amendment filed on Mar. 25, 2013 for U.S. Appl. No. 13/849,797, filed Mar. 25, 2013 (Inventor—G. Deshpande et al.; Applicant—Constar International, Inc.; pp. 1-3).
Preliminary Amendment filed on Oct. 15, 2013 for U.S. Appl. No. 13/849,797, filed Mar. 25, 2013 (Inventor—G. Deshpande et al.; Applicant—Constar International, Inc.; pp. 1-14).
Preliminary Amendment filed on Nov. 21, 2012 for EP Pat. App. No. 10822439.5, national phase of Intl. App. No. PCT/US2010/050719, Sep. 29, 2010 (Inventor—G. Deshpande; Applicant—Constar International, Inc.; pp. 1-15).
Preliminary Amendment filed on Dec. 10, 2009 for EP Pat. App. No. 08795847.6, which is national phase of Intl. App. No. PCT/US2008/063250, filed May 9, 2008 (Inventor—G. Deshpande et al.; Applicant—Constar International, Inc.; pp. 1-5).
Preliminary Amendment dated Oct. 15, 2015 to the U.S. Patent and Trademark Office for U.S. Appl. No. 14/585,413, filed Dec. 30, 2014 (Inventor—Girish N. Deshpande) (pp. 1-9).
Preliminary Amendment dated Apr. 25, 2016 to the U.S. Patent and Trademark Office for U.S. Appl. No. 14/935,953, filed Nov. 9, 2015 (Inventor—Girish N. Deshpande) (pp. 1-23).
Ragusa, A. et al, Novel Enantioselective Receptors for N-Protected; Glutamate and Aspartate, Chemistry—A European Journal, vol. 11, No. 19, Sep. 19, 2005 (Sep. 19, 2005), pp. 5674-5688.
Response to Communication pursuant to Article 94(3) EPC dated Dec. 7, 2015 for EP Pat. App. No. 14150235.1, filed Jan. 6, 2014 (Inventor—G. Deshpande et al.; Applicant—Constar International, Inc.; pp. 1-2).
Requirement for Restriction/Election dated May 7, 2012 for U.S. Appl. No. 12/945,355, filed Nov. 12, 2010 (Inventor—G. Deshpande et al.; Applicant—Constar International, LLC; pp. 1-11).
Requirement for Restriction/Election dated Jun. 12, 2012 for U.S. Appl. No. 12/945,351, filed Nov. 12, 2010 (Inventor—G. Deshpande et al.; Applicant—Constar International, Inc.; pp. 1-10).
Requirement for Restriction/Election dated Oct. 5, 2010 for U.S. Appl. No. 12/117,849, filed May 9, 2008 (Inventor—G. Deshpande et al.; Applicant—Constar International, Inc.; pp. 1-5).
Requirement for Restriction/Election dated Nov. 2, 2012 for U.S. Appl. No. 12/945,353, filed Nov. 12, 2010 (Inventor—G. Deshpande et al.; Applicant—Constar International, Inc.; pp. 1-10).
Requirement for Restriction/Election dated Dec. 20, 2012 for U.S. Appl. No. 12/945,351, filed Nov. 12, 2010 (Inventor—G. Deshpande; Applicant—Constar International, Inc.; pp. 1-8).
Requirement for Restriction/Election dated May 9, 2012 for U.S. Appl. No. 12/893,817, filed Sep. 29, 2010 and published as US 2011-0123741 A1 on May 26, 2011 (Inventor—G. Deshpande et al.; Applicant—Constar International, Inc.; pp. 1-8).
Response after Final Office Action filed on Oct. 7, 2014 for U.S. Appl. No. 12/945,351, filed Nov. 12, 2010 (Inventor—G. Deshpande; Applicant—Constar International, Inc.; pp. 1-7).
Response after Non-Final Office Action filed on Mar. 4, 2014 for U.S. Appl. No. 12/945,351, filed Nov. 12, 2010 (Inventor—G. Deshpande; Applicant—Constar International, Inc.; pp. 1-34).
Response after Non-Final Office Action filed on May 18, 2015 for U.S. Appl. No. 12/945,351, filed Nov. 12, 2010 (Inventor—G. Deshpande; Applicant—Constar International, Inc.; pp. 1-7).
Response after Non-Final Office Action filed on Jun. 4, 2014 for U.S. Appl. No. 13/849,797, filed Mar. 25, 2013 (Inventor—G. Deshpande et al.; Applicant—Constar International, Inc.; pp. 1-17).
Response after Non-Final Office Action filed on Oct. 29, 2013 for U.S. Appl. No. 12/945,353, filed Nov. 12, 2010 (Inventor—G. Deshpande; Applicant—Constar International, Inc.; pp. 1-10).
Response after Non-Final Office Action filed on Apr. 8, 2011 for U.S. Appl. No. 12/117,849, filed May 9, 2008 (Inventor—G. Deshpande et al.; Applicant—Constar International, Inc.; pp. 1-16).
Response to Communication pursuant to Article 94(3) EPC dated Oct. 24, 2014 for EP Pat. App. No. 10830816.4, filed Nov. 12, 2010 and published as 2499134 on Sep. 19, 2012 (Inventor—G. Deshpande et al.; pp. 1-2).
Response to Communication pursuant to Article 94(3) EPC dated Apr. 5, 2016 for EP Pat. App. No. 10830816.4, filed Nov. 12, 2010 and published as 2499134 on Sep. 19, 2012 (Inventor—G. Deshpande et al.; pp. 1-2).
Response to Election/Restriction Requirement filed on Mar. 4, 2013 for U.S. Appl. No. 12/945,353, filed Nov. 12, 2010 (Inventor—G. Deshpande; Applicant—Constar International, Inc.; pp. 1-3).
Response to Election/Restriction Requirement filed on Aug. 7, 2012 for U.S. Appl. No. 12/945,355, filed Nov. 12, 2010 (Inventor—G. Deshpande et al.; Applicant—Constar International, LLC; pp. 1-6).
Response to Election/Restriction Requirement filed on Aug. 10, 2012 for U.S. Appl. No. 12/893,817, filed Sep. 29, 2010 and published as US 2011-0123741 A1 on May 26, 2011 (Inventor—G. Deshpande et al.; Applicant—Constar International, Inc.; pp. 1-2).
Response to Election/Restriction Requirement filed on Dec. 17, 2010 for U.S. Appl. No. 12/117,849, filed May 9, 2008 (Inventor—G. Deshpande et al.; Applicant—Constar International, Inc.; pp. 1-3).
Response to ExParte Quayle Action was mailed on May 5, 2016 to the U.S. Patent and Trademark Office for U.S. Appl. No. 13/849,797, filed Mar. 25, 2013 and published as US-2014-0027339-A1 on Jan. 30, 2014 (Inventor—Girish N. Deshpande) (2 pages).
Response to Final Office Action with Request for Continued Examination filed on Dec. 1, 2014 for U.S. Appl. No. 12/893,817, filed Sep. 29, 2010 (Inventor—G. Deshpande; Applicant—Constar International, Inc.; pp. 1-20).
Response to First Examination Report dated Dec. 10, 2015 for Indian Application No. 7423/DELNP/2009, which was filed on May 9, 2008 (Inventor—G. Deshpande et al.) (pp. 1-262).
Response to Non-Final Office Action filed on Aug. 14, 2013 for U.S. Appl. No. 12/893,817, filed Sep. 29, 2010 and published as US 2011-0123741 A1 on May 26, 2011 (Inventor—G. Deshpande; Applicant—Constar International, Inc.; pp. 1-19).
Response to Office Action filed on Dec. 21, 2011 for CN Pat. App. No. 200880023116.X, which is national phase of Intl. App. No. PCT/US2008/063250, filed May 9, 2008 (Inventor—G. Deshpande et al.; Applicant—Constar International, Inc.; pp. 1-37).
Response to Office Action filed on Feb. 3, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-4).
Response to Office Action filed on Mar. 27, 2012 for CL Pat. App. No. 1391/2008, national phase of Intl. App. No. PCT/US2008/063250, filed May 9, 2008 (Inventor—G. Deshpande et al.; Applicant—Constar International, Inc.; pp. 1-21).
Response to Office Action filed on Aug. 20, 2012 for MX Pat. App. No. MX/a/2009/012183, which is national phase of Intl. App. No. PCT/US2008/063250, filed May 9, 2008 (Inventor—G. Deshpande et al.; Applicant—Constar International, Inc.; pp. 1-2).
Response to Office Action dated Oct. 1, 2015 to the Canadian Patent Office for Canadian Application No. 2687081, which was filed on May 9, 2008 (Inventor—Girish N. Deshpande) (4 pages).
Response to Requirement for Restriction/Election filed on Jun. 20, 2013 for U.S. Appl. No. 12/945,351, filed Nov. 12, 2010 (Inventor—G. Deshpande; Applicant—Constar International, Inc.; pp. 1-3.
Response to Requirement for Restriction/Election filed on Oct. 12, 2012 for U.S. Appl. No. 12/945,351, filed Nov. 12, 2010 (Inventor—G. Deshpande et al.; Applicant—Constar International, Inc.; pp. 1-3).

(56) References Cited

OTHER PUBLICATIONS

Rosevear, J., et al., A Comparison of the Reactions of Some Ethyl N-Arylcarbamates with Those of the Corresponding Acetanilides. II Amidomethylation with N-Hydroxymethylphthalimide, Austr. J. Chem., 1990, vol. 43(2): pp. 339-353.
Rossi, S. et al., A Highly Enantioselective Receptor for N-Protected Glutamate and Anomalous Solvent-Dependent Binding Properties, Angew. Chem. Int. Ed., vol. 41, No. 22, 2002, pp. 4233-4236.
Second Office Action dated Sep. 19, 2016 for Chinese Application No. 2013106426272, which was filed on Dec. 3, 2013 and published as CN104017241 on Sep. 3, 2014 (Inventor—G. Deshpande et al.; Applicant—Constar International, Inc.; Original—4 pages// Translated—7 pages).
Second Office Action dated Mar. 16, 2012 for CN Pat. App. No. 200880023116.X, national phase of Intl. App. No. PCT/US2008/063250, filed May 9, 2008 (Inventor—G. Deshpande et al.; Applicant—Constar International, Inc.; pp, 1-11).
Hara, S. et al., Allylic Polymers, 1: Synthesis of Polyallyl Compounds Containing 4-Oxycarbonylphthalimido Units and Their Polymers, Die Makromolekulare Chemie, 1975, vol. 176(1): pp. 127-141.
Supplementary European Search Report dated Jul. 30, 2013 by the European Patent Office for Application No. 10822439.5, which was filed on Sep. 29, 2010 and published as 2483342 on Aug. 8, 2012 (Inventor—Girish N. Deshpande) (6 pages).
Supplementary European Search Report dated Aug. 27, 2015 by the European Patent Office for Application No. 10830821.4, which was filed on Nov. 12, 2010 and published as 2499182 on Sep. 19, 2012 (Inventor—Girish N. Deshpande) (2 pages).
Third Office Action dated Jan. 5, 2013 for CN Pat. App. No. 200880023116.X, national phase of Intl. App. No. PCT/US2008/063250, filed May 9, 2008 (Inventor—G. Deshpande et al.; Applicant—Constar International, Inc.; pp. 1-11).
Vacca, A. et al., A New Tripodal Receptor for Molecular Recognition of Monosaccharides. A Paradigm for Assessing Glycoside Binding Affinities and Selectivities by 1H NMR Spectroscopy, Journal of the American Chemical Society, 2004, vol. 126(50): pp. 16456-16465.
Yoshito, T. et al., Novel Self-Assembly of m-Xylylene Type Dithioureas by Head-to-Tail Hydrogen Bonding, J. org. Chem., 1998, vol. 63: pp. 7481-7489.
Zhanthin et al., The synthesis of fluorine-containing azamacrocyclic; compounds, Heterocycles, International Journal for Reviews and Communications in Heterocyclic Chemistry, (1992) 34(9):1729-1736.
Examination Report dated Dec. 1, 2016 by the European Patent Office for EP Application No. 2016203377, which was filed on May 4, 2016 and published as (Applicant—Plastipak Packaging, Inc.) (3 pages).
Decision of Refusal dated Jan. 23, 2017 by SIPO for JP Application No. 2015-249201, which was filed on Dec. 22, 2015 (Applicant—Plastipak Packaging, Inc.) (Original 2 pages// Translated 2 pages).
Office Action dated Jan. 16, 2017 by the Canadian Patent Office for CA Application No. 2,779,714, which was filed on Sep. 29, 2010 (Applicant—Plastipak Packaging, Inc.) (3 pages).
Non Final Rejection dated Feb. 8, 2017 by the U.S. Patent and Trademark Office for U.S. Appl. No. 14/935,953, filed Nov. 9, 2015 and published as US-2016-0229988-A1 on Aug. 11, 2016 (Applicant—Plastipak Packaging, Inc.) (20 pages).
Communication pursuant to Article 94(3) EPC dated Dec. 16, 2016 by the European Patent Office for EP Application No. 10830821.4, which was filed on Nov. 12, 2010 and published as 2499182 on Sep. 19, 2012 (Applicant—Plastipak Packaging, Inc.) (6 pages).
Second Office Action dated Mar. 31, 2017 by the Canadian Intellectual Property Office for CA Application No. 2780768, which was filed on Nov. 12, 2010 and published as CA 2780768 A1 on May 19, 2011 (Applicant—Plastipak Packaging, Inc.) (3 pages).
Office Action dated Apr. 13, 2017 by the Russian Patent Office for RU Application No. 2013142425, which was filed on Sep. 17, 2013 and published as RU 2013142425 A on Apr. 10, 2015 (Applicant—Plastipak Packaging, Inc.) (Original—5 pages// Translated—3 pages).
Office Action dated May 23, 2017 by the Canadian Intellectual Property Office for CA Application No. 2780746, which was filed on Nov. 12, 2010 and published as CA 2780746 A1 on May 19, 2011 (Applicant—Plastipak Packaging, Inc.) (3 pages).
Final Rejection dated Jun. 13, 2017 by the USPTO for U.S. Appl. No. 14/585,413, filed Dec. 30, 2014 and published as US 2016-0376404 A1 on Dec. 29, 2016 (Applicant—Plastipak Packaging, Inc.) (3 pages).
Office Action dated Aug. 30, 2017 by the Canadian Intellectual Property Office for Patent Application No. 2779714, which was filed on Sep. 29, 2010 and published on Apr. 14, 2011 (Inventor—Deshpande; Applicant—Plastipak Packaging, Inc.) (3 pages).
Response to Non-Final Office Action filed on Aug. 7, 2017 with the U.S. Patent and Trademark Office for U.S. Appl. No. 12/893,817, filed Sep. 29, 2010 and published as US 2011/0123741 on May 26, 2011 (Inventor—Deshpande; Applicant—Plastipak Packaging, Inc.) (17 pages).
Notice of Allowance dated Sep. 15, 2017 by the U.S. Patent and Trademark Office for U.S. Appl. No. 12/893,817, filed Sep. 29, 2010 and published as US 2011/0123741 on May 26, 2011 (Inventor—Deshpande; Applicant—Plastipak Packaging, Inc.) (10 pages).
Office Action dated Jul. 25, 2017 by the Canadian Intellectual Property Office for Patent Application No. 2780749, which was filed on Nov. 12, 2010 and published on May 19, 2011 (Inventor—Deshpande; Applicant—Plastipak Packaging, Inc.) (3 pages).
Response to Non-Final Office Action filed on Aug. 8, 2017 with the U.S. Patent and Trademark Office for U.S. Appl. No. 14/935,953, filed Nov. 9, 2015 and published as US 2016/0229988 on Aug. 11, 2016 (Inventor—Deshpande; Applicant—Plastipak Packaging, Inc.) (32 pages).
Final Office Action dated Aug. 31, 2017 by the U.S. Patent and Trademark Office for U.S. Appl. No. 14/935,953, filed Nov. 9, 2015 and published as US 2016/0229988 on Aug. 11, 2016 (Inventor—Deshpande; Applicant—Plastipak Packaging, Inc.) (9 pages).
Non-Final Office Action dated Sep. 27, 2017 by the U.S. Patent and Trademark Office for U.S. Appl. No. 15/147,532, filed May 5, 2016 and published as US 2017/0088332 on Mar. 30, 2017 (Inventor—Deshpande et al.; Applicant—Plastipak Packaging, Inc.) (6 pages).
Notice of Appeal filed on Dec. 13, 2017 by the U.S. Patent and Trademark Office for U.S. Appl. No. 14/585,413, filed Dec. 30, 2014 and published as US 2016/0376404 on Dec. 29, 2016 (Inventor—Deshpande et al.; Applicant—Plastipak Packaging, Inc.) (2 pages).
Second Office Action dated Jul. 11, 2017 by the Argentinian Patent Office for Patent Application No. P080102003, which was filed on May 12, 2008 (Inventor—Deshpande et al.; Applicant—Plastipak Packaging, Inc.) (Original—5 pages // Translation—3 pages).
Notice of Acceptance dated Nov. 30, 2017 by the Intellectual Property Office of Australia for Patent Application No. 2016203377, which was filed on May 4, 2016 (Inventor—Deshpande et al.; Applicant—Plastipak Packaging, Inc.) (3 pages).
Certificate of Patent dated Dec. 13, 2017 by the European Patent Office for Patent Application No. 14150235.1, which was filed on Jan. 6, 2014 and issued as 2754690 on Dec. 13, 2017 (Inventor—Deshpande et al.; Applicant—Plastipak Packaging, Inc.) (1 page).
Office Action dated Nov. 3, 2017 by the Intellectual Property Office of Mexico for Patent Application No. MX/a/2013/001496, which was filed on Feb. 6, 2013 (Inventor—Deshpande et al.; Applicant—Plastipak Packaging, Inc.) (Original—4 pages; Translation—2 pages).
Decision to Grant dated Nov. 15, 2017 by the Patent Office of the Russian Federation for Patent Application No. 2013142425, which was filed on Sep. 17, 2013 (Inventor—Deshpande et al.; Applicant—Plastipak Packaging, Inc.) (Original—22 pages; Translation—20 pages).
Issue Notification dated Jan. 31, 2018 by the U.S. Patent and Trademark Office for U.S. Appl. No. 12/893,817, filed Sep. 29, 2010 and published as US 2011/0123741 on May 26, 2011 (Inventor—Deshpande; Applicant—Plastipak Packaging, Inc.) (1 page).
Examination Report No. 1 dated Mar. 24, 2017 by the Intellectual Property Office of Australia for Patent Application No. 2016200734, which was filed on Feb. 5, 2016 and published on Mar. 3, 2016 (Inventor—Deshpande; Applicant—Plastipak Packaging, Inc.) (4 pages).

(56) References Cited

OTHER PUBLICATIONS

Supplementary European Search Report and Opinion dated Dec. 13, 2017 by the European Patent Office for Patent Application No. 10830818.0, which was filed on Dec. 12, 2010 and published as EP2499195 on Sep. 19, 2012 (Inventor—Deshpande; Applicant—Plastipak Packaging, Inc.) (6 pages).
Examination Report No. 1 dated Mar. 24, 2017 by the Intellectual Property Office of Australia for Patent Application No. 2016200891, which was filed on Feb. 11, 2016 and published on Mar. 3, 2016 (Inventor—Deshpande; Applicant—Plastipak Packaging, Inc.) (3 pages).
Office Action dated Nov. 27, 2017 by the Canadian Intellectual Property Office for Patent Application No. 2,780,768, which was filed on Nov. 12, 2010 2016 (Inventor—Deshpande; Applicant—Plastipak Packaging, Inc.) (3 pages).
Intention to Grant dated Nov. 2, 2017 by the European Patent Office for Patent Application No. 10830816.4, which was filed on Nov. 12, 2010 and published as EP2499134 on Sep. 19, 2012(Inventor—Deshpande; Applicant—Plastipak Packaging, Inc.) (6 pages).
Preliminary Amendment filed on Jul. 11, 2016 with the U.S. Patent and Trademark Office for U.S. Appl. No. 14/976,766, filed Dec. 21, 2015 and published as US 2016/0311771 on Oct. 27, 2016 (Inventor—Deshpande; Applicant—Plastipak Packaging, Inc.) (5 pages).
Restriction Requirement dated Dec. 29, 2016 by the U.S. Patent and Trademark Office for U.S. Appl. No. 14/976,766, filed Dec. 21, 2015 and published as US 2016/0311771 on Oct. 27, 2016 (Inventor—Deshpande; Applicant—Plastipak Packaging, Inc.) (7 pages).
Ex Parte Quayle Action issued on Sep. 22, 2017 by the U.S. Patent and Trademark Office for U.S. Appl. No. 14/976,766, filed Dec. 21, 2015 and published as US 2016/0311771 on Oct. 27, 2016 (Inventor—Deshpande; Applicant—Plastipak Packaging, Inc.) (7 pages).
Notice of Allowance dated Apr. 23, 2018 by the U.S. Patent and Trademark Office for U.S. Appl. No. 14/976,766, filed Dec. 21, 2015 and published as US 2016/0311771 on Oct. 27, 2016 (Inventor—Deshpande; Applicant—Plastipak Packaging, Inc.) (8 pages).
Communication Pursuant to Article 94(3) EPC dated Oct. 17, 2018 by the European Office Action for Patent Application No. 10830821.4, which was filed on Nov. 12, 2010 and published as EP 2499182 on Sep. 19, 2012 (Inventor—G.N. Deshpande; Applicant—Plastipak Packaging, Inc.) (5 pages).
Requirement for Restriction/Election dated Apr. 24, 2014 for U.S. Appl. No. 13/889,133, filed May 7, 2013 (Inventor—G. Deshpande et al.; Applicant—Constar International, Inc.; pp. 1-9).
Response to Requirement for Restriction/Election dated 49/24/2014 to the U.S. Appl. No. 13/889,133, filed May 7, 2013 (Inventor—G. Deshpande et al.; Applicant—Constar International, Inc.; pp. 1-9).
Non Final Rejection dated Jan. 15, 2015 for U.S. Appl. No. 13/889,133, filed May 7, 2013 (Inventor—Deshpande et al.; Applicant—Constar International, Inc.; pp. 1-6).
Response to Non Final Rejection dated Jul. 14, 2015 to the U.S. Appl. No. 13/889,133, filed May 7, 2013 (Inventor—G. Deshpande et al.; Applicant—Constar International, Inc.; pp. 1-10).
Notice of Allowance dated Aug. 17, 2015 for U.S. Appl. No. 13/889,133, filed May 7, 2013 (Inventor—G. Deshpande et al.; Applicant—Constar International, Inc.; pp. 1-8).
Issue Notification dated Dec. 9, 2015 for U.S. Appl. No. 13/889,133, filed May 7, 2013 (Inventor—G. Deshpande et al.; Applicant—Constar International, Inc.; p. 1).
U.S. Appl. No. 60/928,553, filed May 10, 2007, Deshpande et al.
U.S. Appl. No. 12/117,849 (7,994,245), filed May 9, 2008 (Aug. 9, 2011), Deshpande et al.
U.S. Appl. No. 13/164,447 (8,431,721), filed Jun. 20, 2011 (Apr. 30, 2013), Deshpande et al.
U.S. Appl. No. 13/849,797 (9,475,630), filed Mar. 25, 2013 (Oct. 25, 2016), Deshpande et al.
U.S. Appl. No. 15/147,532 10,125,096, filed May 5, 2016 (Mar. 30, 2017), Deshpande et al.
U.S. Appl. No. 16/189,363 10,906,870, filed Nov. 13, 2018 (Feb. 2, 2021), Deshpande, et al.
U.S. Appl. No. 61/246,956, filed Sep. 29, 2009, Deshpande.
U.S. Appl. No. 12/893,817 9,896,554, filed Sep. 29, 2010 (Feb. 20, 2018), Deshpande.
U.S. Appl. No. 61/261,158, filed Nov. 13, 2009, Deshpande.
U.S. Appl. No. 12/945,351 (9,181,414), filed Nov. 12, 2010 (Nov. 10, 2015), Deshpande.
U.S. Appl. No. 14/935,953 (10,040,922), filed Nov. 9, 2015 (Aug. 7, 2018), Deshpande.
U.S. Appl. No. 61/261,209, filed Nov. 13, 2009, Deshpande.
U.S. Appl. No. 12/945,353 (8,478,519), filed Nov. 12, 2010 (Jun. 10, 2014), Deshpande.
U.S. Appl. No. 14/258,823 (8,975,345), filed Apr. 22, 2014 (Mar. 10, 2015), Deshpande.
U.S. Appl. No. 14/585,413 10,138,327, filed Dec. 30, 2014 (Nov. 27, 2018), Deshpande.
U.S. Appl. No. 61/261,219, filed Nov. 13, 2009, Deshpande.
U.S. Appl. No. 12/945,355 (8,450,398), filed Nov. 12, 2010 (May 28, 2013), Deshpande.
U.S. Appl. No. 13/889,133 (9,222,020), filed May 7, 2013 (Dec. 29, 2015), Deshpande.
U.S. Appl. No. 14/976,766 (10,059,666), filed Dec. 21, 2015 (Aug. 28, 2018), Deshpande.
U.S. Appl. No. 16/114,737, filed Aug. 28, 2018, Deshpande.

\* cited by examiner

OXYGEN SCAVENGING MOLECULES, ARTICLES CONTAINING SAME, AND METHODS OF THEIR USE

CROSS REFERENCE TO RELATED APPLICATIONS

This Application is a continuation of U.S. application Ser. No. 16/189,363, filed Nov. 13, 2018, which is a continuation of U.S. application Ser. No. 15/147,532, filed May 5, 2016, now issued as U.S. Pat. No. 10,125,096, which is a continuation of U.S. application Ser. No. 13/849,797, filed Mar. 25, 2013, now issued as U.S. Pat. No. 9,475,630, which is a continuation of U.S. application Ser. No. 13/164,477, filed Jun. 20, 2011, now issued as U.S. Pat. No. 8,431,721, which is a division of U.S. application Ser. No. 12/117,849, filed May 9, 2008, now issued as U.S. Pat. No. 7,994,245, which claims the benefit of U.S. Provisional Application No. 60/928,553, filed May 10, 2007, the contents of which are incorporated herein by reference in their entireties.

FIELD OF THE INVENTION

The present invention relates to compounds useful for oxygen scavenging. The invention also relates to substantially transparent compositions that comprise a base polymer, an oxidizable organic component, and a transition metal. The invention also is directed to uses of such compositions in the construction of packaging for oxygen sensitive materials.

BACKGROUND OF THE INVENTION

It is known in the art to include an oxygen scavenger in the packaging structure for the protection of oxygen sensitive materials. Such scavengers are believed to react with oxygen that is trapped in the package or that permeates from outside of the package, thus extending to life of package contents. These packages include films, bottles, containers, and the like. Food, beverages (such as beer and fruit juices), cosmetics, medicines, and the like are particularly sensitive to oxygen exposure and require high barrier properties to oxygen to preserve the freshness of the package contents and avoid changes in flavor, texture and color.

Use of certain polyamides in combination with a transition metal is known to be useful as the oxygen scavenging material. One particularly useful polyamide is MXD6 which contains meta-xylene residues in the polymer chain. See, for example, U.S. Pat. Nos. 5,639,815; 5,049,624; and 5,021,515.

Other oxygen scavengers include potassium sulfite (U.S. Pat. No. 4,536,409), unsaturated hydrocarbons (U.S. Pat. No. 5,211,875), and ascorbic acid derivatives (U.S. Pat. No. 5,075,362).

In barrier layers of packaging walls that are made from blends of oxygen scavenging materials with base polymer resins such as PET, haze can result due to such factors as the immiscibility of the scavenging materials with the base polymer resins and the inability to create by mechanical blending means disperse-phase domains that are so small as not to interfere with the passage of light therethrough; and the adverse influence of the scavenging material on the crystallization behavior of PET base resin. One approach to minimizing such haze is careful selection of base resin to improve dispersibility of the scavenger material and, thus, reduce, but not substantially eliminate, haze; and to minimize the adverse crystallization effect. This approach may undesirably narrowly restrict the choice of base polymer resin. Another approach is to use compositions that serve as compatibilizers to reduce haze. These approaches add cost to the layer and the compatibilizer adds an additional material that must be evaluated for its suitability for contact with food. Thus, there is a need in the art for improved materials which provide high oxygen scavenging capability and are substantially transparent.

SUMMARY OF THE INVENTION

The present invention is directed to compositions comprising:
(a) a base polymer;
(b) at least one compound of Formula I or II

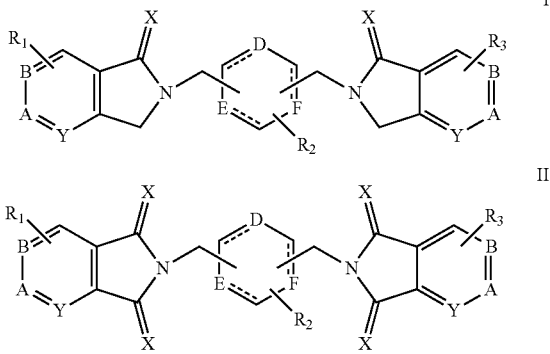

wherein X is selected from the group consisting of O, S and NH; Y, A and B are independently selected from the group consisting of N and CH; D, E and F are independently selected from the group consisting of CH, N, O and S; the symbol ---- when used in conjunction with a bond line represents a single or a double bond; and $R_1$, $R_2$ and $R_3$ are independently selected from the group consisting of H, electron withdrawing groups and electron releasing groups and a transition metal; and (c) at least one transition metal in a positive oxidation state, said metal being present in the composition in an amount of 10 to 400 ppm; wherein said compound is present in an amount of about 0.10 to 10 weight percent of said composition. Methods of preparing, as well as methods of implementing, the compositions of the present invention are also described.

Also within the scope of the present invention are compounds of Formulas I and II. Methods of preparing and using the compounds of Formulas I and II are also described.

DETAILED DESCRIPTION OF ILLUSTRATIVE EMBODIMENTS

Figure 1:
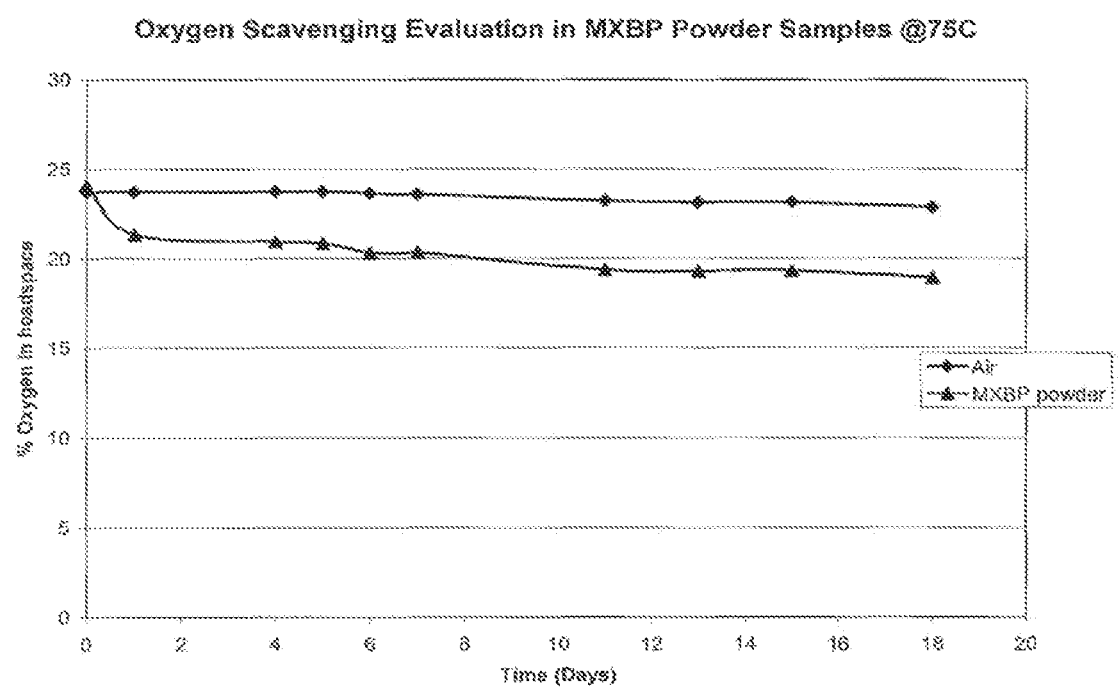
FIG. 1 shows the percent oxygen in a vial containing MXBP, a preferred embodiment of the present invention, over 18 days.

In some embodiments, the invention concerns compounds of Formula I and II:

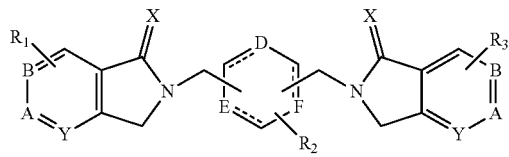

I

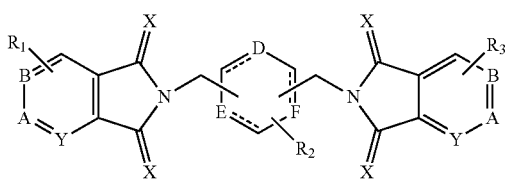

II wherein X is selected from the group consisting of O, S and NH; Y, A and B are independently selected from the group consisting of N and CH; D, E and F are independently selected from the group consisting of CH, N, O and S; the symbol ---- represents a single or a double bond; and $R_1$, $R_2$ and $R_3$ are independently selected from the group consisting of H, electron withdrawing groups and electron releasing groups.

In some aspects, the invention concerns compounds having the formula:

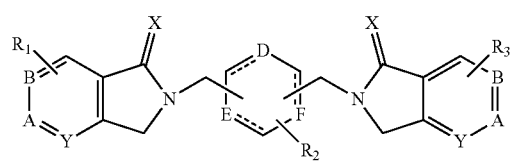

wherein X is O, S or NH; Y, A and B are independently N or CH; D, E and F are independently CH, N, O or S; the symbol ---- in addition to the solid line represents a single or a double bond; and $R_1$, $R_2$ and $R_3$ are independently H, electron withdrawing groups or electron releasing groups.

In some compositions, X is O; Y, A and B are all CH; D, E, and F are all CH; ---- is a double bond; and $R_1$, $R_2$ and $R_3$ are all hydrogen. Certain compositions have the formula

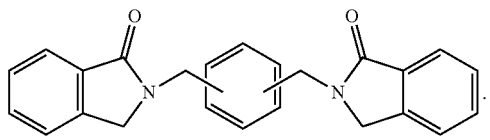

Other compositions have the formula

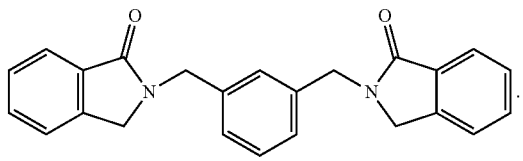 [SMILES: O=C1c2ccccc2CN1Cc1cccc(CN2Cc3ccccc3C2=O)c1]

In other preferred embodiments, X is O; Y is N, A and B are CH; D, E, and F are all CH; ---- is a double bond; and $R_1$, $R_2$ and $R_3$ are all hydrogen. Certain compositions of the present invention have the formula:

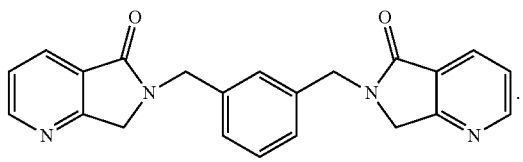 [SMILES: O=C1c2cccnc2CN1Cc1cccc(CN2Cc3ncccc3C2=O)c1]

In yet other embodiments $R_1$ and $R_3$ are electron releasing groups. Electron releasing groups, also known as electron donating groups, are known in the art. Preferred electron releasing groups include branched and straight chain alkyl groups, for example, methyl, ethyl, propyl, isopropyl, butyl, isobutyl, and tert-butyl. Certain preferred compositions of the present invention have the formula:

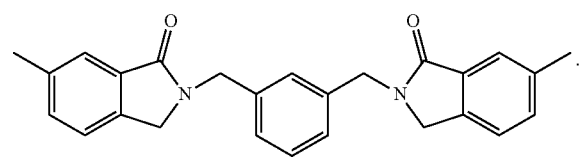

Other preferred electron releasing groups include alkoxy, for example methoxy and ethoxy. Still other preferred electron releasing groups include amines, for example —$NH_2$ and N(loweralkyl)$_2$.

In still other embodiments, $R_1$ and $R_3$ are electron withdrawing groups. Electron withdrawing groups are known in the art. Preferred electron withdrawing groups include nitro, carboxylic acid, esters, for example loweralkyl esters, and cyano. Certain preferred compositions of the present invention have the formula:

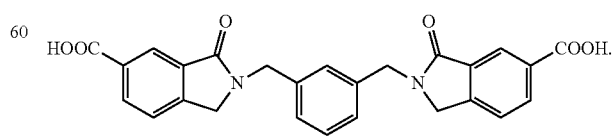

Other preferred compositions of the present invention have the formula:

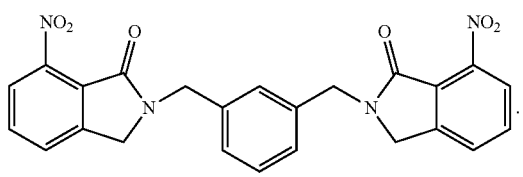 [SMILES: O=C1c2c(cccc2[N+](=O)[O-])CN1Cc1cccc(CN2Cc3cccc([N+](=O)[O-])c3C2=O)c1]

Yet other compositions of the present invention are of the formula:

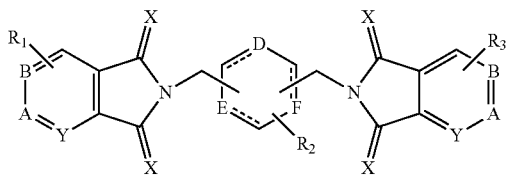

wherein X is O, S or NH; Y, A and B are independently N or CH; D, E and F are independently CH, N, O or S; the symbol ---- in addition to the solid line represents a single or a double bond; and $R_1$, $R_2$ and $R_3$ are independently H, electron withdrawing groups or electron releasing groups. In certain of these compositions, X is O; Y, A and B are all CH; D, E, and F are all CH; ---- is a double bond; and $R_1$, $R_2$ and $R_3$ are all hydrogen.

Other compositions of the invention have the formula

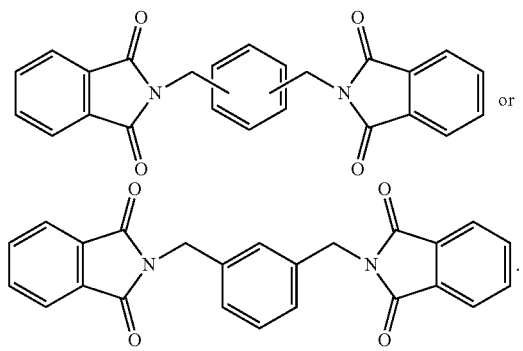

In some aspects, the invention concerns organic material normally susceptible to gradual degradation in the presence of oxygen during use over an extended period containing an antioxidant, or oxygen scavenging, effective amount of a compound disclosed herein.

Some aspects of the invention concern containers comprising a film-forming polymer, having at least one wall comprising an effective amount of an oxygen-scavenging composition comprising a compound disclosed herein.

Other aspects concern oxygen scavenging compositions that react with oxygen in the presence of transition metals and salts thereof comprising an effective amount of a compound disclosed herein. The invention also relates to an oxygen scavenging system comprising: (a) an oxygen scavenging composition comprising a compound of Formula I or II; (b) an effective amount of a transition metal catalyst; and (b) a functional barrier permeable to oxygen.

The invention also relates to compositions comprising (a) a base polymer; (b) at least one compound of Formula I or II; and (c) at least one transition metal in a positive oxidation state, the metal being present in the composition in an amount of 10 to 400 ppm; where the compound is present in an amount of about 0.10 to 10 weight percent of the composition. One preferred transition metal is cobalt. In some embodiments, the at least one transition metal further comprises zinc. In other embodiments, the transition metal comprises zinc and cobalt.

In some compositions, the base polymer comprises a polyester polymer. One preferred polyester polymer is polyethylene terephthalate.

The compound(s) described herein is present in an amount of about 1 to about 10 weight percent based on the weight of the composition in some embodiments. In other embodiments, the oxygen scavenging compound is present in an amount of about 1 to about 5 weight percent based on the weight of the composition. In still other embodiments, the compound is present in an amount of about 1 to about 3 weight percent based on the weight of the composition. Also within the scope of the invention are those embodiments were the compound(s) described herein is present in an amount of about 0.1 to about 10 weight percent based on the weight of the composition.

Some preferred embodiments of the invention have a concentration of transition metal from 30 to 150 ppm of the total composition weight.

Other aspects of the invention concern package walls comprising at least one layer, the layer comprising a composition, the composition comprising: (a) a base polymer; (b) at least one compound of Formula I or II; and (c) at least one transition metal in a positive oxidation state, the metal being present in the composition in an amount of 10 to 400 ppm; wherein the compound is present in an amount of about 0.10 to 10 weight percent of the composition.

Yet other aspects of the invention relate to package walls comprising a composition, the composition comprising: (a) one or more outer layers; and (b) one or more inner layers; wherein at least one of the inner or at least one of the outer layers comprises a composition comprising: (1) a base polymer; (2) at least one compound of formula I or II; and (3) at least one transition metal in a positive oxidation state, the metal being present in the composition in an amount of 10 to 400 ppm; wherein the compound is present in an amount of about 0.10 to 10 weight percent of the composition. In some embodiments, the first layer is disposed radially outward from the second layer.

The invention also relates to methods for packaging an oxygen sensitive material comprising:

(a) preparing a package having a wall comprising at least one layer, at least one of the layers comprising a composition, the composition comprising
    a base polymer;
    at least one compound of Formula I or II; and
    at least one transition metal in a positive oxidation state, the metal being present in the composition in an amount of 10 to 400 ppm; wherein the compound is present in an amount of about 0.10 to 10 weight percent of the composition;

(b) introducing the oxygen sensitive material into the package; and (c) closing the package.

Still other embodiments of the invention concern methods for producing a packaging material having a wall with oxygen barrier properties comprising:

(a) combining a base polymer with at least one compound of formula I or II to form a composition, the composition having at least one transition metal in a positive oxidation state, the metal being present in the composition in an amount of 10 to 400 ppm; and wherein the compound is present in an amount of about 0.10 to 10 weight present of the composition;

(b) forming the product of step (a) into a wall; and (c) forming a container which comprises the wall.

Another aspect of the invention concerns processes for making an article comprising:

(a) forming a melt by combining in a melt processing zone:
    a base polymer,
    at least one compound of formula I or II, and
    at least one transition metal in a positive oxidation state, the metal being present in the composition in an amount of 10 to 400 ppm; wherein the compound is present in an amount of about 0.10 to 10 weight present of the composition;

(b) forming an article from the melt.

In some embodiments, the article is a perform, a sheet, a bottle, a cup, or a jar.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed, for example, in Advanced Organic Chemistry by J. March, 1985, pp. 16-18.

Electron withdrawing groups include fluoro, chloro, bromo, nitro, acyl, cyano, carboxyl, lower alkenyl, lower alkynyl, carboxaldehyde, carboxyamido, aryl, quaternary ammonium, trifluoro-methyl, alkoxycarbonyl, aryloxycarbonyl, aminocarbonyl, sulfonic, alkanesulfonyl, arylsulfonyl, perfluoroalkancsulfonyl, perfluoroarylsulfonyl, phosphoryl, tertiary amine cation and a combination thereof among others.

Electron donating groups include such groups as hydroxy, lower alkoxy, lower alkyl, amino, lower alkylamino, di(lower alkyl)amino, aryloxy, mercapto, lower alkylthio, lower alkylmercapto and disulfide among others. One skilled in the art will appreciate that the aforesaid substituents may have electron donating or electron withdrawing properties under different chemical conditions. Moreover, the present invention contemplates any combination of substituents selected from the above-identified groups.

In some embodiments, the most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkylamino), amine lower mercapto, mercaptoalkyl, alkylthio and alkyldithio.

The antioxidant/oxygen scavenger of the invention can be used in a broad range of organic products normally subject to gradual degradation in the presence of oxygen during use over an extended period. In some embodiments, the organic compositions protected by the present antioxidants are of the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not necessarily flame retarding additives nor flame suppressing.

In some embodiments, the antioxidant/oxygen scavenger can be utilized at elevated temperatures. One such use would be during a melt processing operation.

In some embodiments, the invention relates to synthesis of the compounds of the invention. In a first synthetic scheme about 2 moles of a compound of the formula

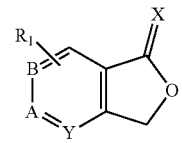

is reacted under reaction conditions to release water, which is trapped in a Dean-Stark trap, with one mole of a compound of the formula

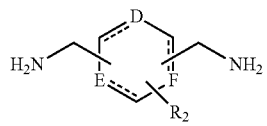

to produce the desired product having the formula:

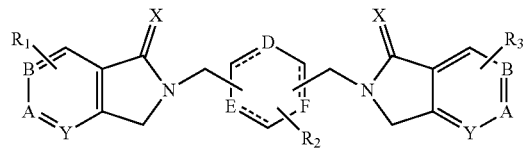

wherein all the groups are as defined above.

In one preferred embodiment, 2 moles of phthalide (also known as o-hydroxymethyl-benzoic acid lactone or 1,3-dihydrobenzo[c]furan-1-one or oxophthalane or 1(3H)-isobenzo-furanone) are reacted with meta-xylylenediamine as shown below:

Scheme 1

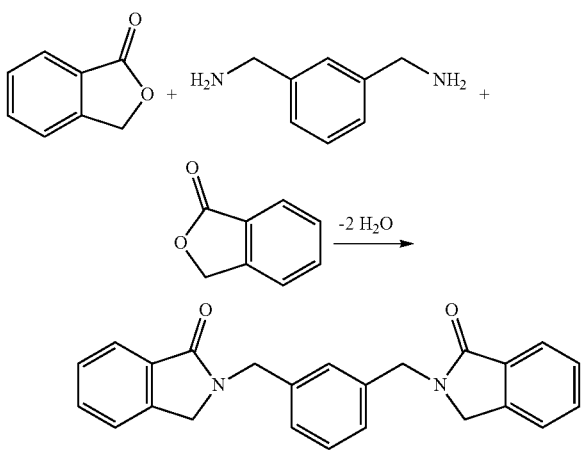

In another synthetic embodiment, phthalic anhydride is reacted with metaxylylene diamine to produce the diimide product and then as shown below:

Scheme 2
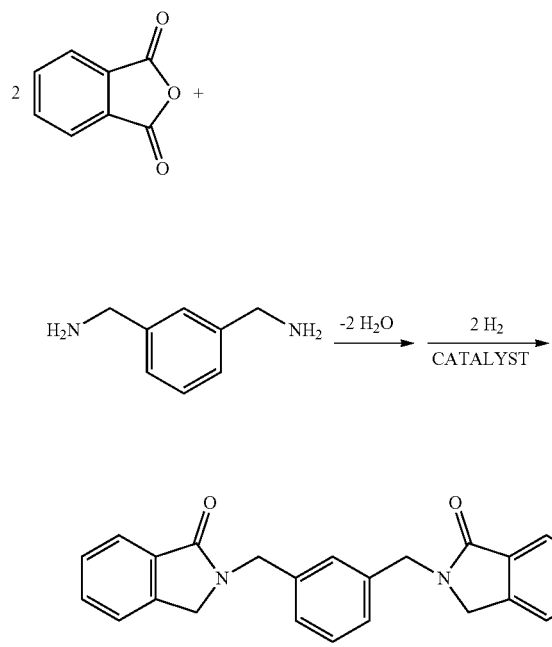
Further embodiments of the present invention can be prepared using methods known generally in the art in accordance with the following Schemes:
Scheme 3
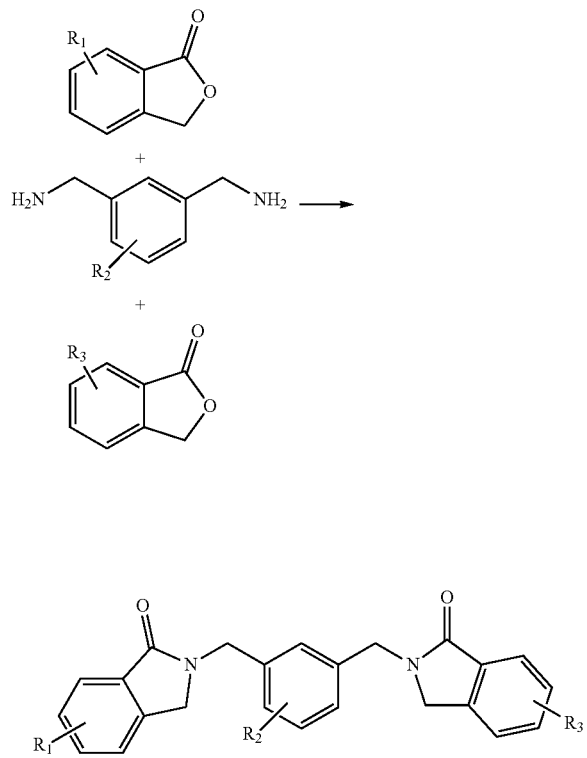
Scheme 4
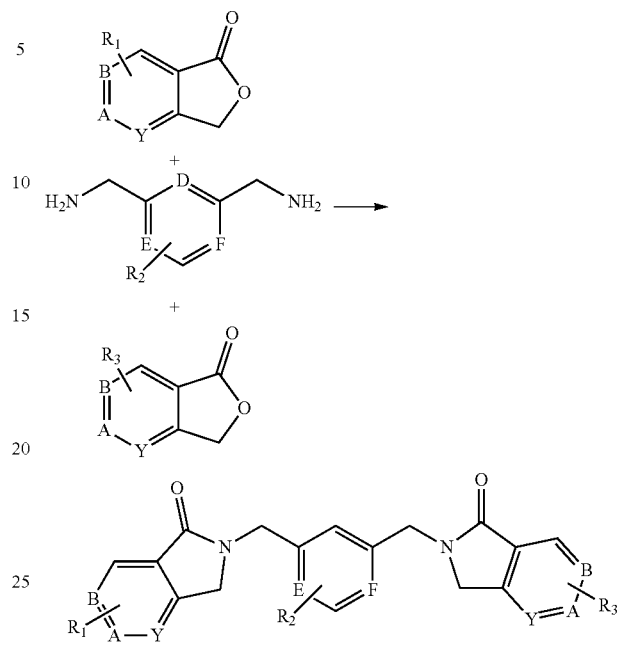
Even further embodiments can be prepared according to the Schemes below:
Scheme 5
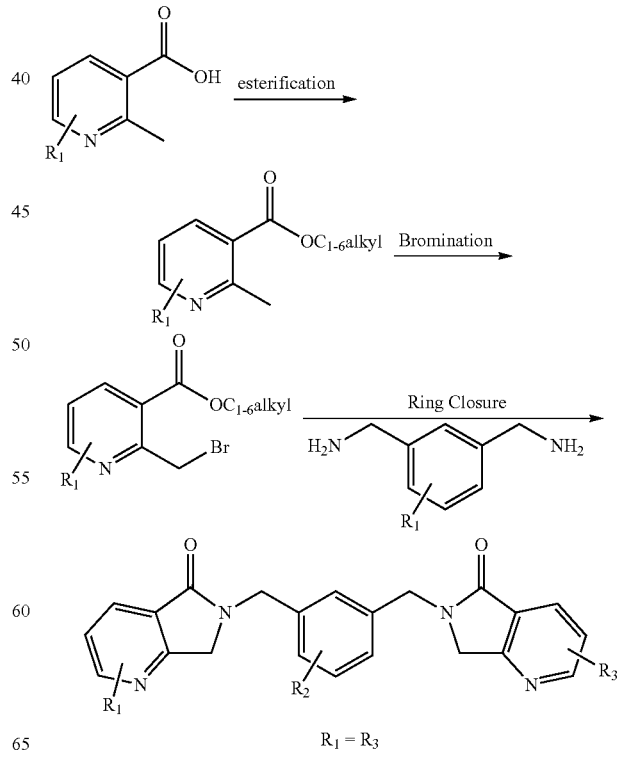

Scheme 6

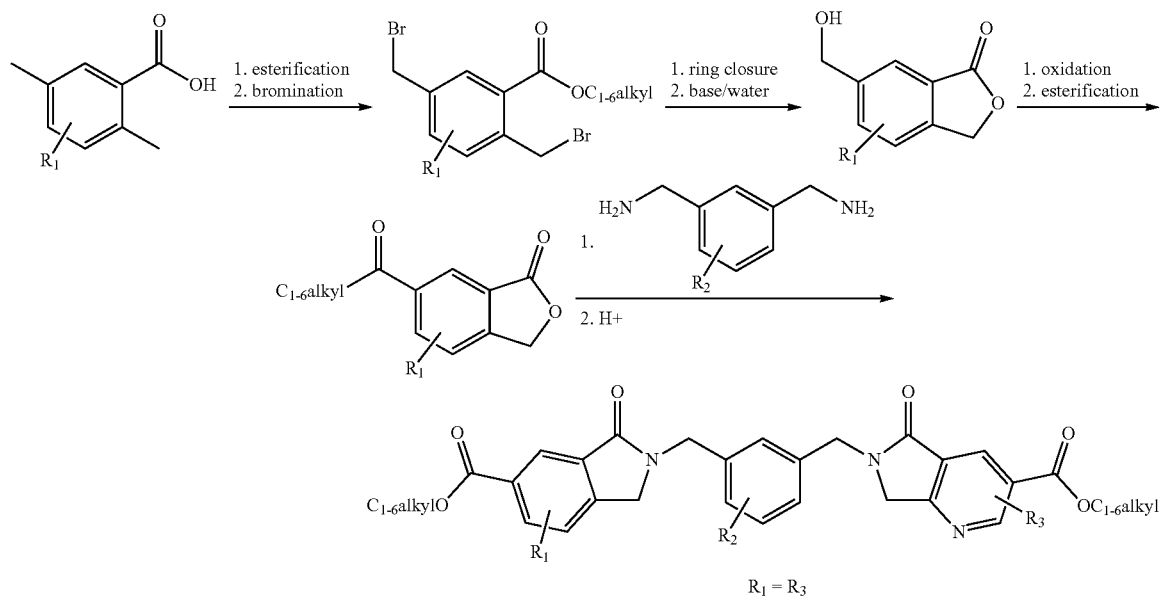

Modifications known in the art can be used to produce further embodiments of the present invention.

Examples of organic materials in which the additives are useful include polymers, both homopolymers and copolymers, of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives provide antioxidant protection in natural and synthetic rubbers such as copolymers of olefinically unsaturated monomers including styrene-butadiene rubber (SBR rubber), ethylenepropylene copolymers, ethylene-propylenediene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylenevinyl acetate copolymers are protected, as are butene-methylacrylate copolymers. Nitrogen-containing polymers such as polyurethanes, nitrite rubber, and lauryl acrylate-vinyl-pyrrolidone copolymers are effectively stabilized. Adhesive compositions such as solutions of polychloroprene (neoprene) in toluene are protected.

Petroleum oils such as solvent-refined, midcontinent lubricating oil and Gulfcoast lubricating oils are effectively stabilized. In hydrocarbon lubricating oils, both mineral and synthetic, the present additives are particularly effective when used in combination with a zinc dihydrocarbyldithiophosphate, e.g. zinc dialkyldithiophosphate or zinc dialkaryldithiophosphate.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear polyesters such as phthalic anhydride-glycol condensates are given a high degree of protection. Polyesters such as those derived from terephthalic acid and alkylene glycols are also given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

The additives can be used to protect any of the many organic substrates to which an antioxidant is normally added. It can be used where economics permit to protect such substrates as asphalt, paper, fluorocarbons such as Teflon®, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

A preferred embodiment of the invention is the incorporation of the oxygen scavenger into polyethylene terephthalate formulations which further include a transition metal catalyst. The oxygen scavenger works particularly well in the presence of the transition metal catalyst.

In combination with the polymer components, the oxygen scavenging compositions including compounds of formula I or II of the present invention may include a transition metal salt, compound or complex, as an oxygen scavenger catalyst. The transition metal can be selected from the first, second, or third transition series of the Periodic Table. The metal can be Rh, Ru, or one of the elements in the series of Sc to Zn (i.e., Sc, Ti, V, Cr, Mn, Fe, Co, Ni, Cu, and Zn). Suitable anions for the salts include, but are not limited to, chloride, acetate, oleate, stearate, palmitate, 2-ethylhexanoate, neodecanoate, and naphthenate. Representative salts include cobalt (II) 2-ethylhexanoate, cobalt oleate, and cobalt (11) neodecanoate. The metal salt also can be an ionomer, in which case a polymeric counter ion may be employed.

The amounts of the components used in the oxygen scavenging formulations of the present invention can affect the use and effectiveness of this composition. Thus, the amounts of polymer, transition metal catalyst, antioxidant, polymeric diluents, additives, etc., can vary depending on the desired article and its end use. For example, one of the primary functions of the polymers described above is to react irreversibly with oxygen during the scavenging process, while a primary function of the transition metal catalyst is to facilitate this process. Thus, to a large extent, the amount of polymer present affects the oxygen scavenging capacity of the composition, i.e., the amount of oxygen that the composition can consume, while the amount of transition metal catalyst affects the rate at which oxygen is consumed as well as the induction period.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cispolybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

The oxygen scavenger composition of the present invention can be incorporated in packaging articles having various forms. Suitable articles include, but are not limited to, flexible sheet films, flexible bags, pouches, semi-rigid and rigid containers such as bottles (e.g. PET bottles) or metal cans, or combinations thereof.

Typical flexible films and bags include those used to package various food items and may be made up of one or a multiplicity of layers to form the overall film or bag-like packaging material. The oxygen scavenger composition of the present invention can be used in one, some or all of the layers of such packaging material.

Typical rigid or semi-rigid articles include plastic, paper or cardboard containers, such as those utilized for juices, soft drinks, as well as thermoformed trays or cup normally having thickness in the range of from 100 to 1000 micrometers. The walls of such articles can comprise single or multiple layers of materials. The articles can also take the form of a bottle or metal can, or a crown, cap, crown or cap liner, plastisol or gasket. The oxygen scavenger composition of the present invention can be used as an integral layer or portion of, or as an external or internal coating or liner of, the formed semi-rigid or rigid packaging article. As a liner, the oxygen scavenger composition can be extruded as a film along with the rigid article itself, in e.g. a coextrusion, extrusion coating, or extrusion lamination process, so as to form the liner in situ during article production; or alternatively can be adhered by heat and/or pressure, by adhesive, or by any other suitable method to an outer surface of the article after the article has been produced.

Although it may be preferable from the standpoint of packaging convenience and/or scavenging effectiveness to employ the present invention as an integral or discrete part of the packaging wall, the invention can also be used as a non-integral component of a packaging article such as, for example, a bottle cap liner, adhesive or non-adhesive sheet insert, sealant, sachet, fibrous mat insert or the like.

Besides articles applicable for packaging food and beverage, articles for packaging other oxygen-sensitive products can also benefit from the present invention. Such products would include pharmaceuticals, oxygen sensitive medical products, corrodible metals or products, electronic devices and the like.

In some embodiments of the invention, the base polymer in the composition is a polyester. In certain embodiments, the polyester polymers of the invention are thermoplastic and, thus, the form of the compositions are not limited and can include a composition in the melt phase polymerization, as an amorphous pellet, as a solid stated polymer, as a semi-crystalline particle, as a composition of matter in a melt processing zone, as a bottle preform, or in the form of a stretch blow molded bottle or other articles. In certain preferred embodiments, the polyester is polyethylene terephthalate (PET).

Examples of suitable polyester polymers include polyethylene terephthalate homopolymers and copolymers modified with one or more polycarboxylic acid modifiers in a cumulative amount of less than about 15 mole %, or about 10 mole % or less, or about 8 mole % or less, or one or more hydroxyl compound modifiers in an amount of less than about 60 mol %, or less than about 50 mole %, or less than about 40 mole %, or less than about 15 mole %, or about 10 mole % or less, or about 8 mole % or less (collectively referred to for brevity as "PET") and polyethylene naphthalate homopolymers and copolymers modified with a cumulative amount of with less than about 15 mole %, or about 10 mole % or less, or about 8 mole % or less, of one or more polycarboxylic acid modifiers or modified less than about 60 mol %, or less than about 50 mole %, or less than about 40 mole %, or less than about 15 mole %, or about 10 mole % or less, or about 8 mole % or less of one or more hydroxyl compound modifiers (collectively referred to herein as "PEN"), and blends of PET and PEN. A modifier polycarboxylic acid compound or hydroxyl compound is a compound other than the compound contained in an amount of at least about 85 mole %. The preferred polyester polymer is polyalkylene terephthalate, and most preferred is PET.

In some embodiments, the polyester polymer contains at least about 90 mole % ethylene terephthalate repeat units, and in other embodiments, at least about 92 mole %, and in yet other embodiments, or at least about 94 mole %, based on the moles of all repeat units in the polyester polymers.

In addition to a diacid component of terephthalic acid, derivates of terephthalic acid, naphthalene-2,6-dicarboxylic acid, derivatives of naphthalene-2,6-dicarboxylic acid, or mixtures thereof, the polycarboxylic acid component(s) of the present polyester may include one or more additional modifier polycarboxylic acids. Such additional modifier polycarboxylic acids include aromatic dicarboxylic acids preferably having about 8 to about 14 carbon atoms, aliphatic dicarboxylic acids preferably having about 4 to about 12 carbon atoms, or cycloaliphatic dicarboxylic acids preferably having about 8 to about 12 carbon atoms. Examples of modifier dicarboxylic acids useful as an acid component(s) are phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like, with isophthalic acid, naphthalene-2,6-dicarboxylic acid, and cyclohexanedicarboxylic acid being most preferable. It should be understood that use of the corresponding acid anhydrides, esters, and acid chlorides of these acids is included in the term "polycarboxylic acid." It is also possible for trifunctional and higher order polycarboxylic acids to modify the polyester.

The hydroxyl component is made from compounds containing 2 or more hydroxyl groups capable of reacting with a carboxylic acid group. In some preferred embodiments, preferred hydroxyl compounds contain 2 or 3 hydroxyl groups. Certain preferred embodiments, have 2 hydroxyl groups. These hydroxyl compounds include $C_2$-$C_4$ alkane diols, such as ethylene glycol, propane diol, and butane diol, among which ethylene glycol is most preferred for container applications. In addition to these diols, other modifier hydroxyl compound component(s) may include diols such as cycloaliphatic diols preferably having 6 to 20 carbon atoms and/or aliphatic diols preferably having about 3 to about 20 carbon atoms. Examples of such diols include diethylene glycol; triethylene glycol; 1,4-cyclohexanedimethanol; propane-1,3-diol and butane-1,4-diol (which are considered modifier diols if ethylene glycol residues are present in the polymer in an amount of at least 85 mole % based on the moles of all hydroxyl compound residues); pentane-1,5-diol; hexane-1,6-diol; 3-methylpentanediol-(2, 4); neopentyl glycol; 2-methylpentanediol-(1,4); 2,2,4-trimethylpentane-diol-(1,3); 2,5-ethylhexanediol-(1,3); 2,2-diethyl propane-diol-(1, 3); hexanediol-(1,3); 1,4-di-(hydroxyethoxy)-benzene; 2,2-bis-(4-hydroxycyclohexyl)-propane; 2,4-dihydroxy-1,1,3,3-tetramethyl-cyclobutane; 2,2-bis-(3-hydroxyethoxyphenyl)-propane; and 2,2-bis-(4-hydroxypropoxyphenyl)-propane. Typically, polyesters such as polyethylene terephthalate are made by reacting a glycol with a dicarboxylic acid as the free acid or its dimethyl ester to produce an ester monomer and/or oligomers, which are then polycondensed to produce the polyester.

In some preferred embodiments, modifiers include isophthalic acid, naphthalenic dicarboxylic acid, trimellitic anhydride, pyromellitic dianhydride, 1,4-cyclohexane dimethanol, and diethylene glycol. The amount of the polyester polymer in the formulated polyester polymer composition ranges from greater than about 50.0 wt. %, or from about 80.0 wt. %, or from about 90.0 wt. %, or from about 95.0 wt. %, or from about 96.0 wt. %, or from about 97 wt. %, and up to about 99.90 wt. %, based on the combined weight of all polyester polymers and all polyamide polymers. The formulated polyester polymer compositions may also include blends of formulated polyester polymer compositions with other thermoplastic polymers such as polycarbonate. In some preferred compositions, the polyester comprises a majority of the composition of the inventions, and in some embodiments the polyester is present in an amount of at least about 80 wt. %, or at least about 90 wt. %, based on the weight of the composition (excluding fillers, inorganic compounds or particles, fibers, impact modifiers, or other polymers serve as impact modifiers or which form a discontinuous phase such as may be found in cold storage food trays).

The polyester compositions can be prepared by polymerization procedures known in the art sufficient to effect esterification and polycondensation. Polyester melt phase manufacturing processes include direct condensation of a dicarboxylic acid with the diol, optionally in the presence of esterification catalysts, in the esterification zone, followed by polycondensation in the prepolymer and finishing zones in the presence of a polycondensation catalyst; or ester exchange usually in the presence of a transesterification catalyst in the ester exchange zone, followed by prepolymerization and finishing in the presence of a polycondensation catalyst, and each may optionally be solid stated according to known methods.

The transition metal used in the instant compositions is a metal in the positive oxidation state. It should be noted that it is contemplated that one or more such metals may be used. In some embodiments, cobalt is added in +2 or +3 oxidation state. In some embodiments, it is preferred to use cobalt in the +2 oxidation state. In certain embodiments, copper in the +2 oxidation state is utilized. In some embodiments, rhodium in the +2 oxidation state is used. In certain embodiments, zinc may also be added to the composition. Preferred zinc compounds include those in a positive oxidation state.

Suitable counter-ions to the transition metal cations include carboxylates, such as neodecanoates, octanoates, acetates, lactates, naphthalates, malates, stearates, acetylacetonates, linoleates, oleates, palmitates, 2-ethylhexanoates, or ethylene glycolates; or as their oxides, borates, carbonates, chlorides, dioxides, hydroxides, nitrates, phosphates, sulfates, or silicates among others.

In some embodiments, levels of at least about 10 ppm, or at least about 50 ppm, or at least about 100 ppm of metal can achieve suitable oxygen scavenging levels. The exact amount of transition metal used in an application can be determined by trials that are well within the skill level of one skilled in the art. In some embodiments involving wall applications (as opposed to master batch applications where more catalyst is used), it is preferred to keep the level of metal below about 300 ppm and, in other embodiments, preferably below about 250 ppm.

The transition metal or metals may be added neat or in a carrier (such as a liquid or wax) to an extruder or other device for making the article, or the metal may be present in a concentrate or carrier with the oxidizable organic component, in a concentrate or carrier with a base polymer, or in a concentrate or carrier with a base polymer/oxidizable organic component blend. Alternatively, at least a portion of the transition metal may be added as a polymerization catalyst to the melt phase reaction for making the base polymer (a polyester polymer in some embodiments) and be present as residual metals when the polymer is fed to the melting zone (e.g. the extrusion or injection molding zone) for making the article such as a preform or sheet. It is desirable that the addition of the transition metal does not substantially increase the intrinsic viscosity (It.V) of the melt in the melt processing zone. Thus, transition metal or metals may be added in two or more stages, such as once during the melt phase for the production of the polyester polymer and again once more to the melting zone for making the article.

The composition may also include other components such as pigments, fillers, crystallization aids, impact modifiers, surface lubricants, denesting agents, stabilizers, ultraviolet light absorbing agents, metal deactivators, nucleating agents such as polyethylene and polypropylene, phosphate stabilizers and dyestuffs. Other additional components are well known to those skilled in the art and can be added to the existing composition so long as they do not negatively impact the performance of the compositions. Typically, the total quantity of such components will be less than about 10% by weight relative to the whole composition. In some embodiments, the amount of these optional components is less than about 5%, by weight relative to the total composition.

A common additive used in the manufacture of polyester polymer compositions used to make stretch blow molded bottles is a reheat additive because the preforms made from the composition must be reheated prior to entering the mold for stretch blowing into a bottle. Any of the conventional reheat additives can be used, such additives include various forms of black particles, e.g. carbon black, activated carbon, black iron oxide, glassy carbon, and silicon carbide; the gray particles such as antimony, and other reheat additives such as silicas, red iron oxide, and so forth.

Other typical additives, depending on the application, are impact modifiers. Examples of typical commercially available impact modifiers well-known in the art and useful in this invention include ethylene/acrylate/glycidyl terpolymers and ethylene/acrylate copolymers in which the acrylate is a methyl or ethyl acrylate or methyl or ethyl methacrylate or the corresponding butyl acrylates, styrene based block copolymers, and various acrylic core/shell type impact modifiers. The impact modifiers may be used in conventional amounts from about 0.1 to about 25 weight percent of the overall composition and, in some embodiments, preferably in amounts from about 0.1 to about 10 weight percent of the composition.

In many applications, not only are the packaging contents sensitive to the ingress of oxygen, but the contents may also be affected by UV light. Fruit juices and pharmaceuticals are two examples of such contents. Accordingly, in some embodiments, it is desirable to incorporate into the polyester composition any one of the known UV absorbing compounds in amounts effective to protect the packaged contents.

The instant compositions can be made by mixing a base polymer (PET, for example) with the oxidizable organic component and the transition metal composition. Such compositions can be made by any method known to those skilled in the art. In certain embodiments, some or part of the transition metal may exist in the base polymer prior to mixing. This residual metal, for example, can exist from the manufacturing process of the base polymer. In some embodiments, the base polymer, the oxidizable organic component and the transition metal are mixed by tumbling in a hopper. Other optional ingredients can be added during this mixing process or added to the mixture after the aforementioned mixing or to an individual component prior to the aforementioned mixing step.

The instant composition can also be made by adding each ingredient separately and mixing the ingredients prior melt processing the composition to form an article. In some embodiments, the mixing can be just prior to the melt process zone. In other embodiments, one or more ingredients can be premixed in a separate step prior to bringing all of the ingredients together.

In some embodiments, the invention concerns use of the compositions described herein as a component of a wall that is used in a package for oxygen sensitive materials. The necessary scavenging capacity of a package will generally have to be greater for walls that have a greater permeance in the absence of scavenging additives. Accordingly, a good effect is harder to achieve with inherently higher permeance materials are used.

The wall may be a rigid one, a flexible sheet, or a clinging film. It may be homogenous or a laminate or coated with other polymers. If it is laminated or coated, then the scavenging property may reside in a layer of the wall the permeance of which is relatively high in the absence of scavenging and which alone would not perform very satisfactorily but which performs satisfactorily in combination with one or more other layers which have a relatively low permeance but negligible or insufficient oxygen-scavenging properties. A single such layer could be used on the outside of the package since this is the side from which oxygen primarily comes when the package is filled and sealed. However, such a layer to either side of the scavenging layer would reduce consumption of scavenging capacity prior to filling and sealing.

When the instant compositions are used in a wall or as a layer of a wall, the permeability of the composition for oxygen is advantageously not more than about 3.0, or about 1.7, or about 0.7, or about 0.2, or about 0.03 $cm^3$ mm/($m^2$ atm day). The permeability of the composition provided by the present invention is advantageously not more than about three-quarters of that in the absence of oxygen-scavenging properties. In some embodiments, the permeability is not more than about one half, one-tenth in certain embodiments, one twenty-fifth in other embodiments, and not more than one-hundredth in yet other embodiments of that in the absence of oxygen-scavenging properties. The permeability in the absence of oxygen-scavenging properties is advantageously not more than about 17 $cm^3$ mm/($m^2$ atm day), or about 10, and or about 6. A particularly good effect can be achieved for such permeabilities in the range from about 0.5, or about 1.0, to 10, or about 6.0, $cm^3$ mm/($m^2$ atm day). Measurements of oxygen permeation can be made by methods described, for example, in U.S. Pat. No. 5,639,815, the contents of which are incorporated herein in its entirety.

In another aspect, the instant composition can be used as a master batch for blending with a polymer or a polymer containing component. In such compositions, the concentration of the oxidizable organic component and the transition metal will be higher to allow for the final blended product to have suitable amounts of these components. The master batch may also contain an amount of the polymer to which the master batch is to be blended with. In other embodiments, the master batch may contain a polymer that is compatible with the polymer that the master batch is to be blended with.

In yet another aspect, the compositions of the instant invention can be used for forming a layer of a wall which primarily provides oxygen-scavenging (another layer including polymer providing gas barrier without significant scavenging), or as a head-space scavenger (completely enclosed, together with the package contents, by a package wall). Such techniques are well know to those skilled in the art. Persons familiar with oxygen scavenging technology and products will understand how to implement the structures disclosed in this paragraph.

The time period for which the permeability is maintained can be extended by storing the articles in sealed containers or under an inert atmosphere such as nitrogen prior to use with oxygen sensitive materials.

In another aspect, the invention provides a package, whether rigid, semi-rigid, collapsible, lidded, or flexible or a combination of these, comprising a wall as formed from the compositions described herein. Such packages can be formed by methods well known to those skilled in the art.

Among the techniques that may be used to make articles are moulding generally, injection moulding, stretch blow moulding, extrusion, thermoforming, extrusion blow moulding, and (specifically for multilayer structures) co-extrusion and lamination using adhesive tie layers. Orientation, e.g. by stretch blow moulding, of the polymer is especially attractive with phthalate polyesters because of the known mechanical advantages that result.

The melt processing zone for making the article can be operated under customary conditions effective for making the intended articles, such as preforms, bottles, trays, and other articles mentioned below. In one embodiment, such conditions are effective to process the melt without substantially increasing the It.V. of the melt and which are ineffective to promote transesterification reactions. In some preferred embodiments, suitable operating conditions effective to establish a physical blend of the polyester polymer, oxidizable organic component, and transition metal are temperatures in the melt processing zone within a range of about 250° C. to about 300° C. at a total cycle time of less than about 6 minutes, and typically without the application of vacuum and under a positive pressure ranging from about 0 psig to about 900 psig. In some embodiments, the residence time of the melt on the screw can range from about 1 to about 4 minutes.

Specific articles include preforms, containers and films for packaging of food, beverages, cosmetics, pharmaceuticals, and personal care products where a high oxygen barrier is needed. Examples of beverage containers are bottles for holding water and carbonated soft drinks, and the invention is particularly useful in bottle applications containing juices, sport drinks, beer or any other beverage where oxygen detrimentally affects the flavor, fragrance, performance (prevent vitamin degradation), or color of the drink. The compositions of the instant invention are also particularly useful as a sheet for thermoforming into rigid packages and films for flexible structures. Rigid packages include food trays and lids. Examples of food tray applications include dual ovenable food trays, or cold storage food trays, both in the base container and in the lidding (whether a thermoformed lid or a film), where the freshness of the food contents can decay with the ingress of oxygen. The compositions of the instant invention also find use in the manufacture of cosmetic containers and containers for pharmaceuticals or medical devices.

The package walls of the instant invention can be a single layer or a multilayer constructions. In some embodiments using multilayer walls, the outer and inner layers may be structural layers with one or more protective layers containing the oxygen scavenging material positioned there between. In some embodiments, the outer and inner layers comprise and polyolefin or a polyester. In certain embodiments, a single layer design is preferred. Such a layer may have advantages in simplicity of manufacture and cost.

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "a", "an", "the" and the like refer to both the singular and plural unless the context clearly indicates otherwise. "A bottle", for example, refers to a single bottle or more than one bottle.

Also as used herein, the description of one or more method steps does not preclude the presence of additional method steps before or after the combined recited steps. Additional steps may also be intervening steps to those described. In addition, it is understood that the lettering of process steps or ingredients is a convenient means for identifying discrete activities or ingredients and the recited lettering can be arranged in any sequence.

Where a range of numbers is presented in the application, it is understood that the range includes all integers and fractions thereof between the stated range limits. A range of numbers expressly includes numbers less than the stated endpoints and those in-between the stated range. A range of from 1-3, for example, includes the integers one, two, and three as well as any fractions that reside between these integers.

As used herein, "master batch" refers to a mixture of base polymer, oxidizable organic component, and transition metal that will be diluted, typically with at least additional base polymer, prior to forming an article. As such, the concentrations of oxidizable organic component and transition metal are higher than in the formed article.

The following examples are included to demonstrate preferred embodiments of the invention regarding synthesis of the molecules and use of the molecules to scavenge oxygen as well products containing such scavengers. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

2 g of MXBP is placed in a 22 cc vial having an oxygen sensitive oxydot on the sidewall of the vial. The vial is sealed such that there is no exchange with the outside environment. A sealed, empty air vial was used as control.

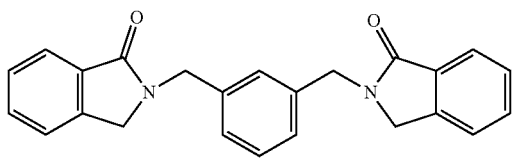

m-xylene bis-phthalimide (MXBP)

Initial percent oxygen levels in the vials are measured at room temperature (~22° C.) using an Oxysense instrument (Oxysense, Inc., Las Vegas, Nev.). The vials are then placed in an air-circulated oven at 75° C. After 1 day in the oven, the vials are removed, cooled to room temperature, and measured for percent oxygen levels. After measurement of 5 oxygen levels, the vials are returned to the 75° C. oven. This procedure is repeated for 18 days. Data generated from these measurements is shown in FIG. 1.

As seen in FIG. 1, MXBP scavenges approximately 4% of oxygen after 18 days.

Example 2

PET resin (Vitiva™, Eastman Chemical Company, Kingsport, Tenn.) is dried in a Piovan Dryer (Model # DSN 520 HE, Piovan Canada, Mississauga, Ontario), at 170° C. for 4 hours (dew point of air used=−50° C.) prior to being fed to an injection molding machine. Moisture content of the resin (after 4 hrs/170° C.) is measured by a Mark 2 HP Moisture analyzer (Sartorious Omnimark Instrument Corp., Temp, Ariz.). The moisture content of the dried PET is approximately 33 ppm.

Cobalt containing polyester (Masterbatch) (4000 ppm Cobalt) is dried in a Dri Air Model RH 15 dryer (Dri-Air Industries, Inc., East Windsor, Conn.) at 291° F. for 3 hours.

A mixture of 2.5 wt % MXBP powder, 2 wt % Cobalt Masterbatch, and 95.5 wt % Vitiva is blended in a bucket. The mixture is poured in the feed hopper of a Husky LX160 injection molding machine (two-cavity, 160 tonnes clamping pressure, Husky Injection Molding Systems Ltd., Novi, Mich.) to produce preforms. The preforms made from this mixture are for a 16 oz. stock hot fill (36 gram preform weight) bottle. The preforms are blown into a bottle on a Sidel SBO 2/3 blow molding machine (Sidel Inc., Norcross, Ga.).

A portion of the Monomer MXBP bottle sidewall was analyzed for cobalt and nitrogen content at Gas Technology Institute, Des Plaines, Ill. Cobalt levels are determined to be approximately 67 ppm and the nitrogen content is approximately 0.11 ppm. This corresponds to approximately 1.45 weight percent of MXBP in the bottle wall.

Example 3—Preparation of QC (Reference)

A preform containing nylon MXD6 (1.5%, based on total weight of preform), cobalt masterbatch (2%, based of total weight of preform), in PET is prepared. The preform is then ground up and used as a control during oxygen scavenging testing.

Example 4

Approximately two weeks after being blown, six bottles prepared according to Example 2 are placed on an Illiop oxygen transmission measuring machine (Constar International, Inc., Philadelphia, Pa.) to measure oxygen transmission rate. The steady state oxygen permeation rate for all the bottles was found to be approximately 0.0005 cc/pkg/day (see Table 1).

TABLE 1

| | Bottle No. | | | | | |
|---|---|---|---|---|---|---|
| | 15 | 17 | 18 | 19 | 20 | 21 |
| Equilibrium Transmission Rate (mL/pkg/day) | 0.0005 | 0.0007 | 0.0004 | 0.0004 | 0.0004 | 0.0005 |

Example 5

PET resin (Vitiva™, Eastman Chemical Company, Kingsport, Tenn.) is dried in a Nissei dryer at 170° C. for 4 hours prior to use. Cobalt containing polyester (Masterbatch) (4000 ppm Cobalt) is dried for approximately 2 hours at 350° F. prior to use.

Plaques (approximately 33.5 gram weight) are molded on 30-ton BOY 22S injection molding machine using the following settings:

| | |
|---|---|
| Barrel temperature | 264° C. |
| Nozzle heater setting | 35% of the power used to heat the barrel |
| Sprue heater set temperature | approx. 215° C. |
| Injection pressure mold | 600 psi (20 sec. of hold pressure; 15 sec. cooling time) |

The mold is water cooled with process water flow rate at approximately 0.5 LPM.

MXBP powder (25.09 g) is hand blended in a bucket with dried Masterbatch (20.09 g) and dried PET (958.4 g). This mixture is poured in the feed hopper of the BOY 22S machine.

The first 10 plaques are discarded as change-over plaques. After the first 10 plaques are discarded, 8 plaques are collected for oxygen scavenging evaluation. Data generated from oxygen scavenging evaluation is shown in FIG. 2.

Figure 2:
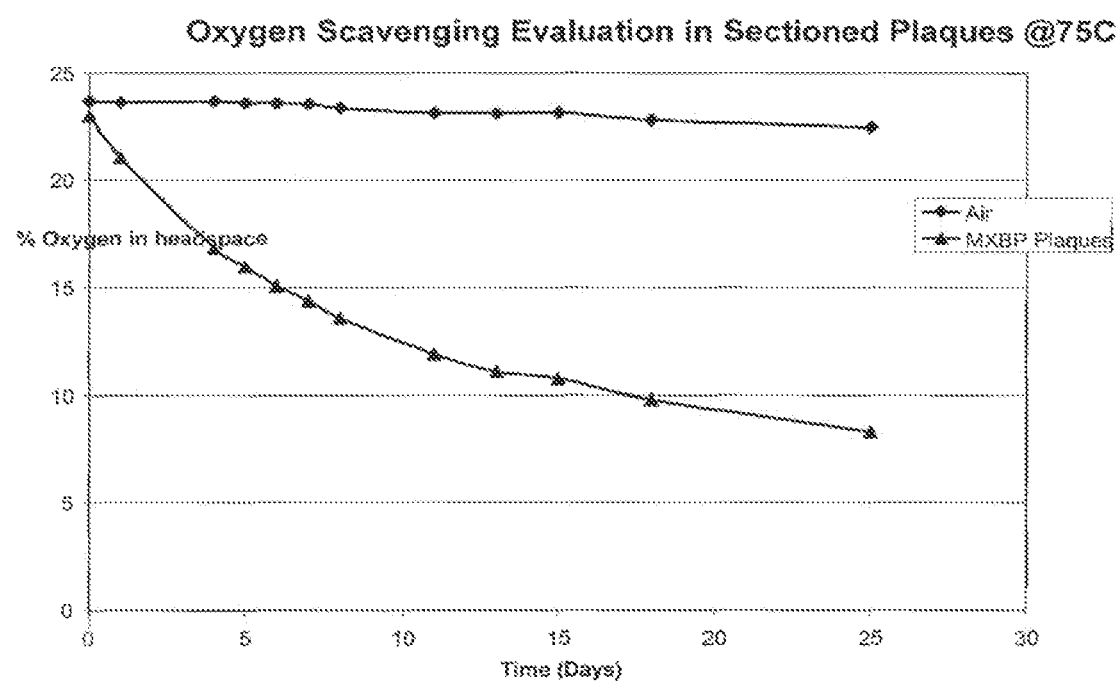
FIG. 2 shows that PET based plaques made with MXBP, preferred embodiments of the present invention, scavenge approximately 14% of oxygen in an enclosed environment after 25 days.

As seen in FIG. 2, PET plaques containing MXBP scavenge approximately 14% of oxygen after 25 days.

Example 6 Preparation of MXBP

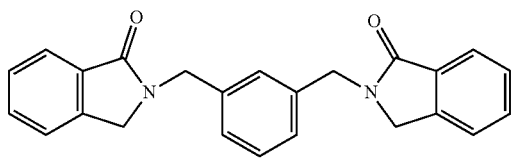

m-xylene bis-phthalimide (MXBP)

To phthalide 674.1 g. (5.026 mol) heated to 115° C. was added m-xylylenediamine 325.9 g (2.393 mol) with nitrogen sparge. The solution was heated to 190° C. and held for 1.5 hours during which time 20 mL of water distillate was collected in a Dean-Stark trap. The heat was then increased to 200° C. and held for 3.5 hours during which time an additional 23 mL of water was collected. The heat was then was increased to 210° C. and held for 12 hours during which time an additional 15 mL of water was collected. The amine value by titration with 0.1 N perchloric acid in glacial acetic acid was 28.1 mg KOH/gram of sample. Reaction was held an additional 7 hours at 215° C. during which time an additional 2 mL of water was collected and the amine value had dropped to 18.1 mg KOH/gram of sample. This solution was cooled to 125° C. and 1-methyl-2-pyrrolidinone 500 grams was added. The solution was cooled to 90° C. and poured into water 4 L containing glacial acetic acid 40 g with mixing to create a slurry. This was filtered to yield 1000 g of press cake. This was added to isopropanol (IPA) 1000 g and water 2000 g and the resulting slurry was filtered to yield 1000 g of press cake. This was added to IPA 2200 g and the resulting slurry was filtered to yield 1600 g of press cake. This was added to IPA 1500 g and the resulting slurry was filtered to yield 1350 g of press cake. This was added to IPA 1300 g and the resulting slurry was filtered to yield 1240 g of press cake. This was dried at 60° C. to yield 671 g (73.4% yield) of product. Its melting point was 154-157° C. The amine value was less than 0.5 mg KOH/gram of sample. The infrared spectra was consistent with the desired product.

Example 7 Alternative Preparation of MXBP

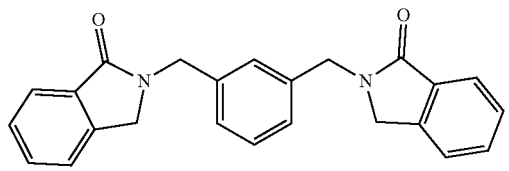 [SMILES: O=C1c2ccccc2CN1Cc1cccc(CN2Cc3ccccc3C2=O)c1]

To phthalide 505.6 g (3.769 mol) heated to 115° C. was added m-xylylenediamine 244.4 g (1.795 mol) with nitrogen sparge. The solution was heated to 180° C. and held for 3.5 hours during which time 14 mL of water distillate was collected in a Dean-Stark trap. The heat was then increased to 190° C. and held for 20 hours during which time an additional 15 mL of water was collected. The amine value was 47 mg KOH/gram of sample. The heat was then increased to 205° C. and held for 7 hours during which time an additional 22 mL of water was collected. The amine value was 30 mg KOH/gram of sample. The heat was then increased to 210° C. and held for 15 hours during which time an additional 5 mL of water was collected. The amine value was 11.7 mg KOH/gram of sample. The solution was cooled to 185° C. and cast into an aluminum tray to yield 661.7 g of a clear, amber solid. This was purified as shown in the following examples.

Example 8—Purification Methods for MXBP

Method A

To IPA 450 g and 1-methyl-2-pyrrolidinone 180 g was added the product of Example 6 330 g and the mixture was heated to 90° C. to produce a clear solution. This was poured into water 2000 mL and IPA 500 g to create a slurry. This was filtered and washed with IPA 300 g to yield 495 g of press cake. This was added to IPA 2500 g and filtered to yield 495 g press cake. This was added to IPA 1500 g and filtered to yield 455 g of press cake. This was dried at 60° C. to yield 219 g (66.4% yield) of the desired product.

Method B

To xylene 247 g was added the product of Example 6 165 g and the mixture was heated to 140° C. to produce a clear solution. The solution was cooled to 50° C. and xylene 100 g was added. The resulting slurry was cooled to 30° C. This was filtered and washed with xylene 200 g to yield 203 g of press cake. This was added to IPA 800 g and heated to 80° C. to produce a clear solution. The solution was cooled to 36° C. and IPA 200 g was added. The resulting slurry was cooled to 30° C. and held 0.5 hours. This was filtered and washed with IPA 200 g to yield 232 g of press cake. This was air dried at ambient temperature to yield 110 g (66.7% yield) of the desired product.

Method C

To IPA 700 g was added the product of Example 6 140 g and the mixture was heated to 80° C. to produce a clear solution. The solution was cooled to 32° C. and IPA 200 g was added. The resulting slurry was cooled to 30° C. and held 0.5 hours. This was filtered and washed with IPA 200 g to yield 220 g press cake. This was added to IPA 600 g and heated to 80° C. to produce a clear solution. This was cooled to 39° C. and IPA 200 g was added. The resulting slurry was cooled to 30° C. and held 0.5 hours. This was filtered and washed with IPA 200 g to yield 232 g of press cake. This was air dried at ambient temperature to yield 105 g (75.0% yield) of the desired product.

Example 9

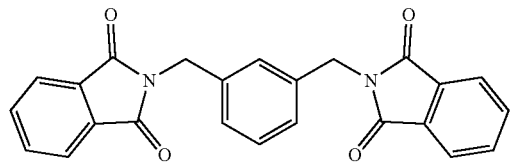 [SMILES: O=C1c2ccccc2C(=O)N1Cc1cccc(CN2C(=O)c3ccccc3C2=O)c1]

To a solution of 1-methyl-2-pyrrolidinone 280 g, xylene 420 g and phthalic anhydride 487.2 g (3.289 mol) heated to 120° C. was added m-xylylenediamine 213.3 g (1.566 mol) over 10 minutes during which time the temperature increased to 145° C. The solution was held at 140° C. for 1 hours during which time 55.0 mL of water distillate was collected in a Dean-Stark trap. The solution was heated to 150° C. during which time an additional 5.0 mL of water was collected and the amine value was 1.4 mg KOH/gram of sample. The resulting slurry was poured into an aluminum tray. The cooled product was added to IPA 1000 g and the resulting slurry was filtered and washed with IPA 200 g. The press cake was added to IPA 1000 g and the resulting slurry was filtered and washed with IPA 200 g. The press cake was air dried at ambient temperature to yield 601.1 g (97.0% yield) of the desired product. Its melting point was 243-248° C. The infrared spectra was consistent with the desired product.

Example 10—Compound 306

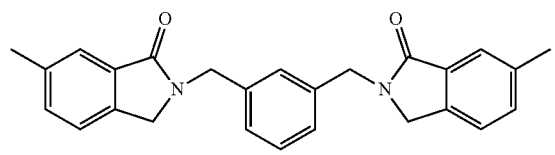

Step 1: Methyl-(2.5-dimethyl)benzoate

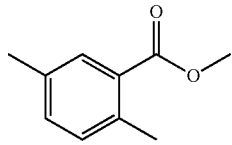

Into a suspension of 75 g (499 mmol) 2,5-dimethylbenzoic acid, 103 g (748 mmol) potassium carbonate in 500 mL of DMF was added dropwise 77.9 g (549 mmol) of iodomethane with stirring at ambient temperature. After addition, the suspension was stirred for additional 5 hours. The reaction mixture was then poured into water and extracted with ethyl acetate. The organic layer was washed with water and brine and dried over anhydrous sodium sulfate. All solids were removed by filtration and the filtrate was concentrated to 80 g of colorless oil as product in 97.6% yield. $^1$H NMR (CDCl$_3$) (300 MHz) δ 2.7 (s, 3H), 2.8 (s, 3H), 3.95 (s, 3H), 7.45 (s 1H), 7.51 (d, $^3$JHCCH=7.9 Hz, 1H), 7.42 (d, $^3$JHCCH=7.9 Hz, 1H)

Step 2: Methyl-di(2,5-bromomethyl)benzoate

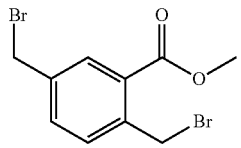

Into a mixture of 80 g (487 mmol) of methyl-(2,5-dimethyl)nitrobenzoate, 95.4 g (503 mmol) of N-bromosuccinimide in 500 mL of carbon tetrachloride was added 121 mg (0.5 mmol) of benzoyl peroxide at 80° C. Heating continued for 16 hours and cooled to ambient temperature. The reaction mixture was then washed with saturated sodium bicarbonate and brine. The organic layer was dried over anhydrous sodium sulfate. All solids were removed by filtration and the filtrate was concentrated to a total of 152 g yellowish solid in 96.9% yield. $^1$H NMR (CDCl$_3$) (300 MHz) δ 3.95 (s, 3H), 4.49 (s, 2H), 4.96 (s, 2H), 7.49 (s 1H), 7.54 (d, $^3$JHCCH=7.9 Hz, 1H), 7.47 (d, 3JHCCH=7.9 Hz, 1H).

Step 3: 6-bromomethylphthalide

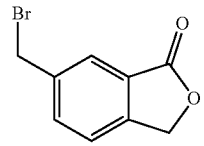

A neat sample of 152 g (472 mmol) of methyl-di(2,5-bromomethyl)benzoate was heated to 120° C. in a slight vacuum. The yellowish solid melted at 80° C. After 16 hours of heating, the reaction mixture was cooled to ambient temperature. Upon cooling, a total of 107 g light brown solid was obtained as product in quantitative yield. $^1$H NMR (CDCl$_3$) (300 MHz) δ 4.58 (s, 2H), 5.30 (s, 2H), 7.49 (s 1H), 7.54 (d, $^3$JHCCH=7.9 Hz, 1H), 7.47 (d, $^3$JHCCH=7.9 Hz, 1H)

Step 4: 6-methylphthalide

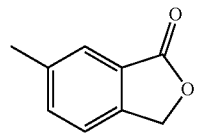

A total of 107 g (472 mmol) of 6-bromomethylphthalide was dissolved in 50 mL of methanol (dioxane was also used in different experiment). The solution was added to a parr bottle with 40 g (540 mmol) of calcium hydroxide and 2 g of 10% Pd/C. The suspension was hydrogenated at 40 psi until no more hydrogen uptake was recorded. All solids were filtered and filtrate was concentrated to a total of 67 g of brown solid in 96% yield. $^1$H NMR (CDCl$_3$) (300 MHz) δ 2.53 (s, 3H), 5.30 (s, 2H), 7.49 (s 11H), 7.54 (d, $^3$JHCCH=7.9 Hz, 1H), 7.47 (d, $^3$JHCCH=7.9 Hz, 1H)

Step 5: 1,3-Bis[(6-methyl-2,3-dihydro-isoindol-1-one-2-yl)methyl]benzene

A mixture of 67 g (452 mmol) 6-methylphthalide and 30.7 g (226 mmol) xylyldiamine was heated to 180° C. with a short path distillation setup to remove water. Upon 170°-180° C., water was collected. After 16 hours of heating at 180° C., heating was stopped and reaction mixture was dissolved in 200 mL of dimethylforamide. The DMF solution was then added dropwise with stirring into 1.5 L of water to precipitate out a total of 73 g of brownish solid. The solid was then recrystallized with methanol to give 55 g of product in 61% yield. $^1$H NMR (DMSO-d$^6$) (500 MHz) δ 2.54 (s, 6H), 4.29 (s, 4H), 4.79 (s, 4H), 7.20 (dd, $^3$JHCCCH=7.6 Hz, $^4$JHCCCH=1.4 Hz, 2H), 7.28 (dd, $^3$JHCCH=7.6 Hz, 1H), 7.30 (s, 11H) 7.66 (dd, $^4$JHCCH=1.4 Hz, JHCCCH=0.65 Hz, 2H), 7.56 (dd, $^3$JHCCH=7.9 Hz, $^4$JHCCCH=0.65 Hz, 2H'), 7.60 (dd, $^3$JHCCH=7.9 Hz, $^4$JHCCCH=1.4 Hz, 2H).

Preparation of Plaques

PET resin (Vitiva™, Eastman Chemical Company, Kingsport, Tenn.) is dried in a Nissei dryer at 170° C. for 4 hours prior to use. Cobalt containing polyester (Masterbatch) (4000 ppm Cobalt) is dried for approximately 2 hours at 350° F. prior to use.

Plaques (approximately 33.5 gram weight) are molded on 30-ton BOY 22S injection molding machine using the following settings:

| | |
|---|---|
| Barrel temperature | 264° C. |
| Nozzle heater setting | 35% of the power used to heat the barrel |
| Sprue heater set temperature | approx. 215° C. |
| Injection pressure mold | 600 psi (20 sec. of hold pressure; 15 sec. cooling time) |

The mold is water cooled with process water flow rate at approximately 0.5 LPM.

Compound 306 (19 g) is hand blended in a bucket with dried Masterbatch (19 g) and dried PET (912 g). This mixture is poured in the feed hopper of the BOY 22S machine.

The first 10 plaques are discarded as change-over plaques. After the first 10 plaques are discarded, 8 plaques are collected for oxygen scavenging evaluation. Data generated from oxygen scavenging evaluation is shown in FIG. 3.

Figure 3:
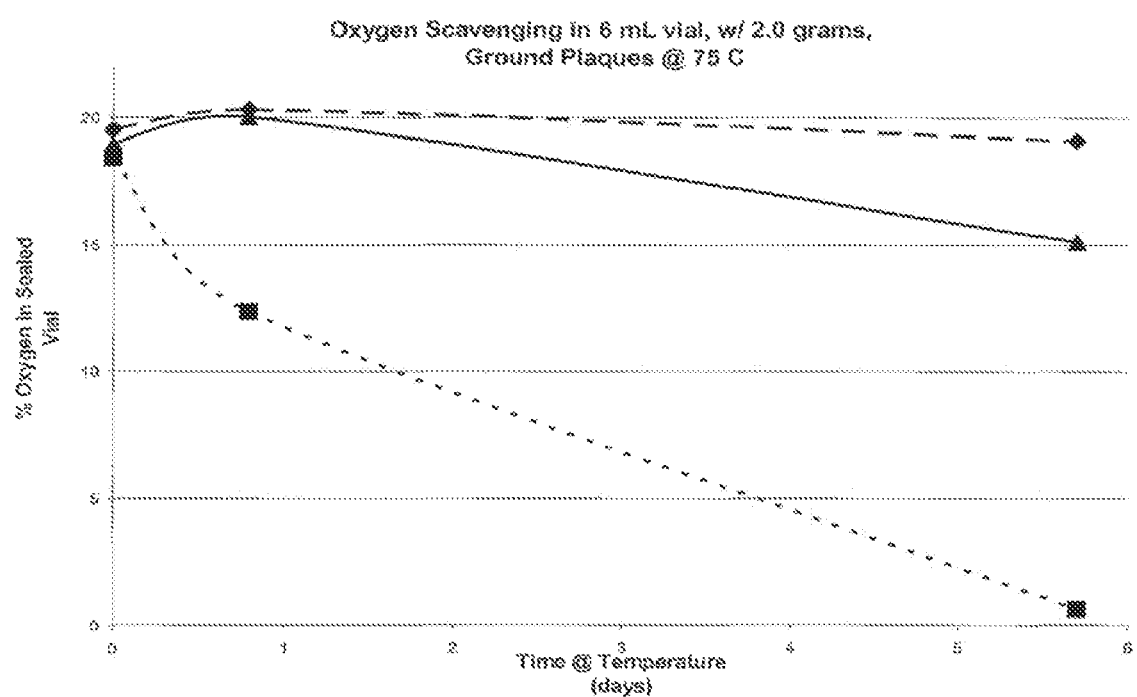
FIG. 3 Oxygen transmission data for Compound 306, a preferred embodiment of the present invention. ■=QC (reference sample comprising 1.5% MXD6, 2% cobalt masterbatch (cobalt neodecanoate in PET); ▲=2'% Compound 306+2% Cobalt Masterbatch+Vitiva; ♦=air.

As seen in FIG. 3, PET plaques containing Compound 306 scavenge approximately 3.9% of oxygen after 5.5 days.

Example 11—Compound 307

1,3-Bis[(isoindole-1,3-dione-2-vi)methyl]benzene

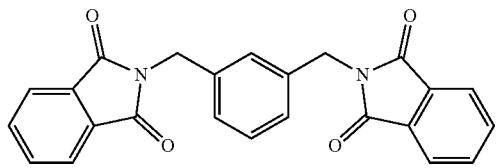 [SMILES: O=C1c2ccccc2C(=O)N1Cc1cccc(CN2C(=O)c3ccccc3C2=O)c1]

Into a suspension of 100 g (675 mmol) of phthalic anhydride, 46 g (338 mmol) of xylyldiamine and 500 mL of glacial acetic acid was heated to 100° C. After 2 hours of heating, the reaction mixture was a clear solution. Heating continued for additional 22 hours. Upon cooling, white suspension was observed. The white solid was filtered and recrystallized with acetic acid to give 126.6 g of a white product in 94.5% yield. 1H NMR (DMSO-$d_6$) (500 MHz) δ 4.74 (s, 4H), 7.19 (dd, 3JHCCCH=7.7 Hz, $^4$JHCCCH=1.5 Hz, 2H), 7.23 (s, 1H), 7.28 (dd, $^3$JHCCCH=7.7 Hz, 1H), 7.86 (unresolved complex, 8H).

Preparation of Plaques

PET resin (Vitiva™, Eastman Chemical Company, Kingsport, Tenn.) is dried in a Nissei dryer at 170° C. for 4 hours prior to use. Cobalt containing polyester (Masterbatch) (4000 ppm Cobalt) is dried for approximately 2 hours at 350° F. prior to use.

Plaques (approximately 33.5 gram weight) are molded on 30-ton BOY 22S injection molding machine using the following settings:

| | |
|---|---|
| Barrel temperature | 264° C. |
| Nozzle heater setting | 35% of the power used to heat the barrel |
| Sprue heater set temperature | approx. 215° C. |
| Injection pressure mold | 600 psi (20 sec. of hold pressure; 15 sec. cooling time) |

The mold is water cooled with process water flow rate at approximately 0.5 LPM.

Compound 307 (38 g) is hand blended in a bucket with dried Masterbatch (19 g) and dried PET (893 g). This mixture is poured in the feed hopper of the BOY 22S machine.

The first 10 plaques are discarded as change-over plaques. After the first 10 plaques are discarded, 8 plaques are collected for oxygen scavenging evaluation. Data generated from oxygen scavenging evaluation is shown in FIG. 5.

Figure 5:
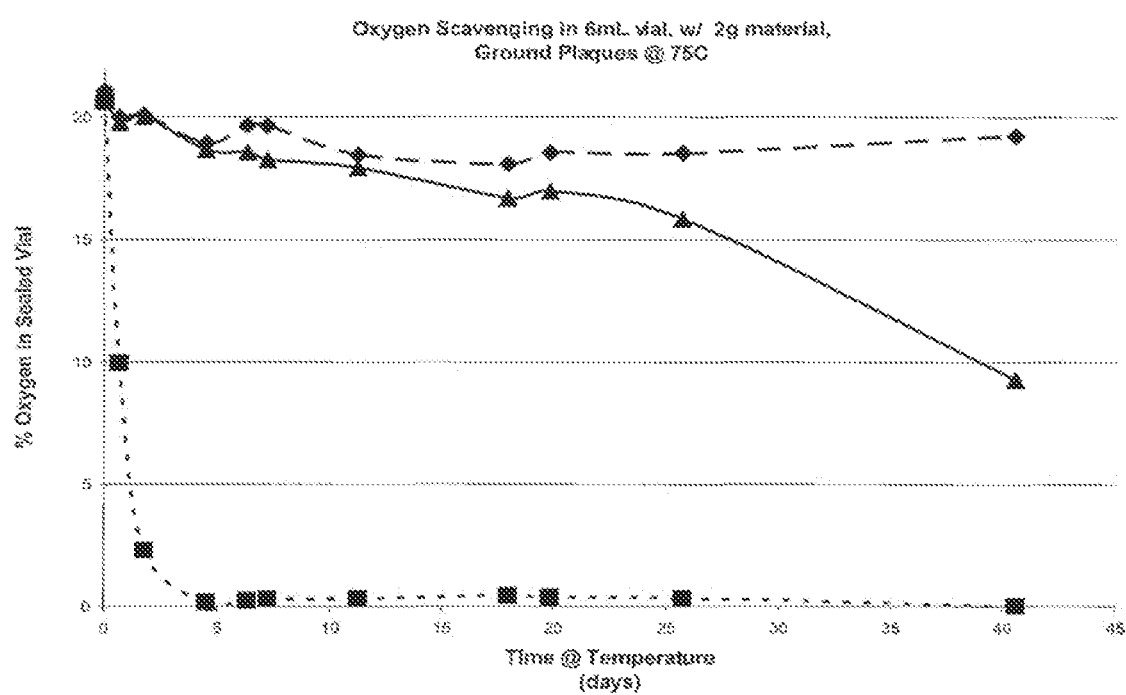
FIG. 5 Oxygen transmission data for Compound 307, a preferred embodiment of the present invention. ■=QC (reference sample comprising 1.5% MXD6, 2% cobalt masterbatch (cobalt neodecanoate in PET); ▲=4% Compound 307+2% Cobalt Masterbatch+Vitiva; ♦=air.

As seen in FIG. 5, PET plaques containing Compound 307 scavenge approximately 4% of oxygen after 25 days.

Example 12—Compound 310

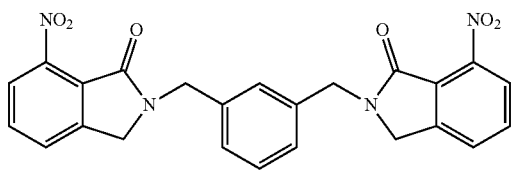 [SMILES: O=C1c2c(cccc2[N+](=O)[O-])CN1Cc1cccc(CN2Cc3cccc([N+](=O)[O-])c3C2=O)c1]

Step 1: Methyl-(2-methyl-6-nitro)benzoate

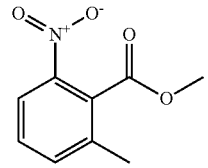

Into a suspension of 100 g (552 mmol) of 2-methyl-6-nitrobenzoic acid, 114.4 g (828 mmol) of potassium carbonate in 500 mL of dimethylformamide was added dropwise 86 g (606 mmol) of iodomethane with stirring at ambient temperature. After addition, the suspension was stirred for additional 5 hours. The reaction mixture was then poured into water and extracted with ethyl acetate. The organic layer was washed with water and brine and dried over anhydrous sodium sulfate. Any solid was removed by filtration and the filtrate was concentrated to a 105.6 g of colorless oil as product in 98% yield. $^1$H NMR (CDCl$_3$) (300 MHz) δ 2.7 (s, 3H), 3.95 (s, 3H), 8.01 (d, $^3$JHCCH=8.6 Hz, 1H), 7.62 (dd, $^3$JHCCH=8.6 Hz, $^3$JHCCH=7.6 Hz, 1H), 7.8 (d, $^3$JHCCH=7.6 Hz, 1H)

Step 2: Methyl-(2-bromomethyl-6-nitro)benzoate

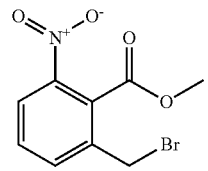

Into a mixture of 100 g (512 mmol) of methyl-(2-methyl-6-nitro)benzoate, 100.2 g (563 mmol) of N-bromosuccinimide in 500 mL of carbon tetrachloride was added 121 mg (0.5 mmol) of benzoyl peroxide at 80° C. Heating continued for 16 hours and cooled to ambient temperature. The reaction mixture was then washed with saturated sodium bicarbonate and brine. The organic layer was dried over anhydrous sodium sulfate. All solids were removed by filtration and the filtrate was concentrated to a total of 137.5 g of yellowish oil in 98% yield. $^1$H NMR (CDCl$_3$) (300 MHz) δ 3.95 (s, 3H), 4.96 (s, 2H) 8.01 (d, $^3$JHCCH=8.6 Hz), 7.62 (dd, $^3$JHCCH=8.6 Hz, 3JHCCH=7.6 Hz), 7.85 (d, $^3$JHCCH=7.6 Hz)

Step 3: 1,3-Bis[(7-nitro-2.3-dihydro-isoindol-1-one-2-yl)methyl]benzene

Into a solution of 80 g (292 mmol) of methyl-(2-bromomethyl-6-nitro)benzoate, 19.9 g (146 mmol) of Xylyldiamine, 32.4 g (320 mmol) triethylamine and 300 mL of methanol was heated to reflux for 24 hours. Upon cooling, the mixture was diluted with ethyl acetate and washed with diluted hydrochloric acid and brine. The organic layer was dried over anhydrous sodium sulfate. All solids were removed by filtration and filtrate was concentrated to 61 g of a yellowish solid. Methanol was used to recrystallize the yellowish solid to yield a total of 87 g of product in 65% yield. $^1$H NMR (DMSO-$d_6$) (500 MHz) δ 4.47 (s, 4H), 4.72 (s, 4H), 7.22 (dd, $^3$JHCCCH=7.5 Hz, $^4$JHCCCH=1.6 Hz, 2H), 7.26 (s, 1H), 7.36 (dd, $^3$JHCCCH=7.5 Hz, 1H), 7.79 (dd, $^3$JHCCCH=7.6 Hz, $^3$JHCCCH=7.6 Hz, 2H), 7.84 (dd, $^3$JHCCCH=7.6 Hz, $^4$JHCCCH=1.0 Hz, 2H), 7.89 (dd, $^3$JHCCCH=7.6 Hz, $^4$JHCCCH=1.0 Hz, 2H).

Preparation of Plaques

PET resin (Vitiva™, Eastman Chemical Company, Kingsport, Tenn.) is dried in a Nissei dryer at 170° C. for 4 hours prior to use. Cobalt containing polyester (Masterbatch) (4000 ppm Cobalt) is dried for approximately 2 hours at 350° F. prior to use.

Plaques (approximately 33.5 gram weight) are molded on 30-ton BOY 22S injection molding machine using the following settings:

| | |
|---|---|
| Barrel temperature | 264° C. |
| Nozzle heater setting | 35% of the power used to heat the barrel |
| Sprue heater set temperature | approx. 215° C. |
| Injection pressure mold | 600 psi (20 sec. of hold pressure; 15 sec. cooling time) |

The mold is water cooled with process water flow rate at approximately 0.5 LPM.

Compound 310 (23.8 g) is hand blended in a bucket with dried Masterbatch (19 g) and dried PET (908 g). This mixture is poured in the feed hopper of the BOY 22S machine.

The first 10 plaques are discarded as change-over plaques. After the first 10 plaques are discarded, 8 plaques are collected for oxygen scavenging evaluation. Data generated from oxygen scavenging evaluation is shown in FIG. 4.

Figure 4:
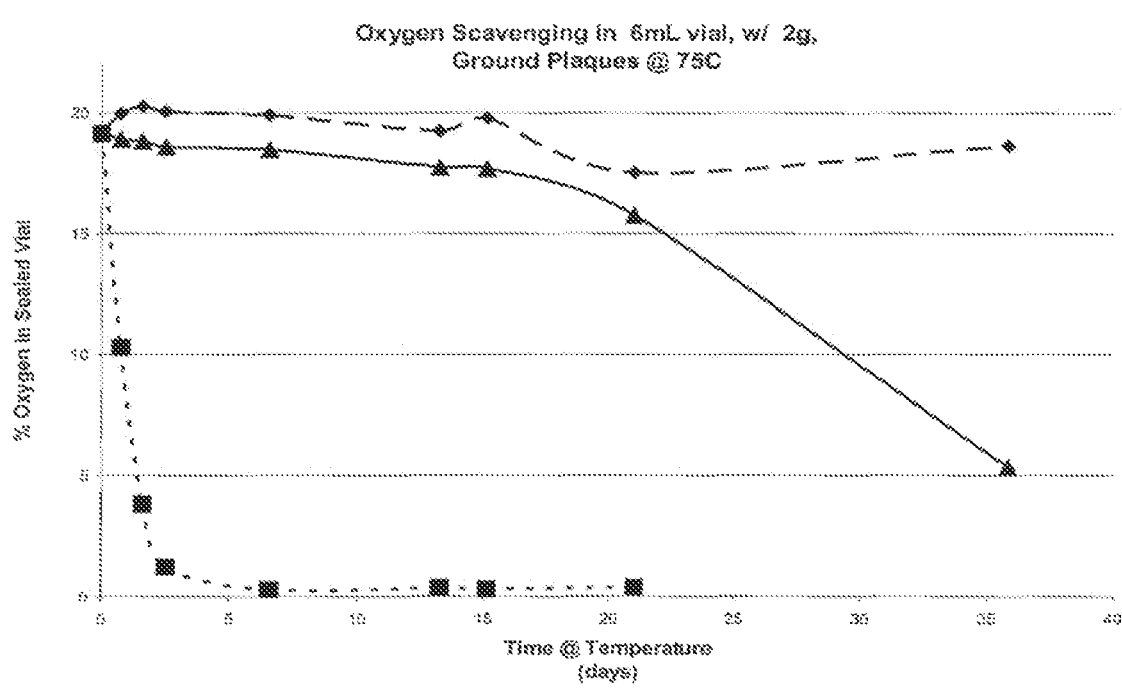
FIG. 4 Oxygen transmission data for Compound 310, a preferred embodiment of the present invention. ■=QC (reference sample comprising 1.5% MXD6, 2% cobalt masterbatch (cobalt neodecanoate in PET); ▲=2.5% Compound 310+2% Cobalt Masterbatch+Vitiva; ♦=air.

As seen in FIG. 4, PET plaques containing Compound 310 scavenge approximately 5% of oxygen after 25 days.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed:

1. A composition comprising organic material normally susceptible to gradual degradation in the presence of oxygen during use over an extended period containing an antioxidant effective amount of a compound of the Formula I or II:

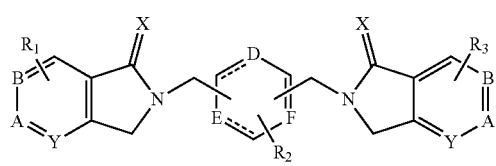

I

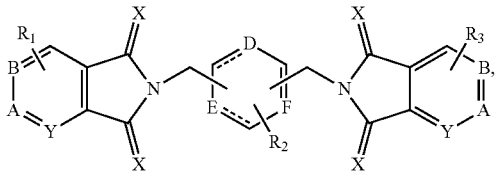

II wherein X is selected from the group consisting of O, S, and NH;
wherein Y, A, and B are independently selected from the group consisting of N and CH;
wherein D, E, and F are independently selected from the group consisting of CH, N, O, and S;
wherein the symbol ---- represents a single or a double bond; and
wherein $R_1$, $R_2$, and $R_3$ are independently selected from the group consisting of H, electron withdrawing groups, and electron releasing groups.

2. An oxygen scavenging composition that reacts with oxygen in the presence of transition metals and salts thereof comprising an effective amount of a compound of the Formula I or II:

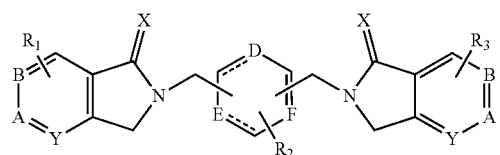

I

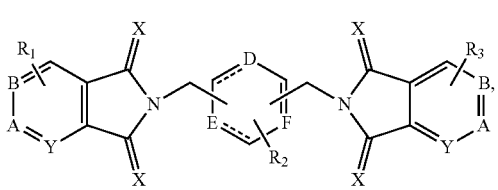

II wherein X is selected from the group consisting of O, S, and NH;
wherein Y, A, and B are independently selected from the group consisting of N and CH;
wherein D, E, and F are independently selected from the group consisting of CH, N, O, and S;
wherein the symbol ---- represents a single or a double bond; and
wherein $R_1$, $R_2$, and $R_3$ are independently selected from the group consisting of H, electron withdrawing groups, and electron releasing groups.

3. An oxygen scavenging system comprising:
(a) an oxygen scavenging composition comprising a compound of the Formula I or II:

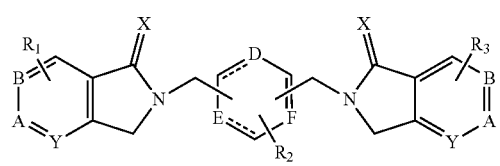

I

-continued

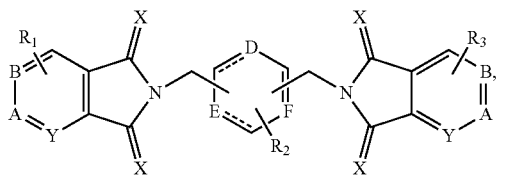

II wherein X is selected from the group consisting of O, S, and NH;
wherein Y, A, and B are independently selected from the group consisting of N and CH;
wherein D, E, and F are independently selected from the group consisting of CH, N, O, and S;
wherein the symbol ---- represents a single or a double bond; and
wherein $R_1$, $R_2$, and $R_3$ are independently selected from the group consisting of H, electron withdrawing groups, and electron releasing groups;
(b) an effective amount of a transition metal catalyst; and
(c) a functional barrier permeable to oxygen.

* * * * *